US009205133B2

(12) United States Patent
Dawson et al.

(10) Patent No.: US 9,205,133 B2
(45) Date of Patent: Dec. 8, 2015

(54) **THERAPEUTIC FOR TREATING *CLOSTRIDIUM DIFFICILE* INFECTION**

(71) Applicant: London School of Hygiene and Tropical Medicine, London (GB)

(72) Inventors: Lisa Dawson, London (GB); Brendan Wren, London (GB)

(73) Assignee: London School of Hygiene and Tropical Medicine, London (GB)

( * ) Notice: Subject to any disclaimer, the term of this patent is extended or adjusted under 35 U.S.C. 154(b) by 0 days.

(21) Appl. No.: 14/402,389

(22) PCT Filed: May 8, 2013

(86) PCT No.: PCT/GB2013/051187
§ 371 (c)(1),
(2) Date: Nov. 20, 2014

(87) PCT Pub. No.: WO2013/175172
PCT Pub. Date: Nov. 28, 2013

(65) Prior Publication Data
US 2015/0104489 A1 Apr. 16, 2015

(30) Foreign Application Priority Data

May 21, 2012 (GB) .................................. 1208879.5

(51) Int. Cl.
| | | |
|---|---|---|
| *A61K 38/46* | (2006.01) | |
| *A61K 45/06* | (2006.01) | |
| *A01N 43/90* | (2006.01) | |
| *C11D 3/48* | (2006.01) | |
| *C11D 3/386* | (2006.01) | |

(52) U.S. Cl.
CPC ............. *A61K 38/465* (2013.01); *A01N 43/90* (2013.01); *A61K 45/06* (2013.01); *C11D 3/38636* (2013.01); *C11D 3/48* (2013.01); *C12Y 301/21* (2013.01); *C12Y 301/21001* (2013.01); *C12Y 301/21002* (2013.01)

(58) Field of Classification Search
CPC .. C07K 14/33; C07K 14/195; C07K 16/1282; A61K 38/00; A61K 39/00; A61K 38/465; A61K 45/06; C12Q 1/689; C12N 9/1051
USPC ........ 424/130.1, 190.1, 409, 85.2, 85.5, 85.6, 424/85.7, 94.2, 94.6; 435/220, 23, 252.3, 435/252.33, 6, 69.3, 6.15, 91.2, 23.2, 24.3, 435/24.33
See application file for complete search history.

(56) References Cited

U.S. PATENT DOCUMENTS

2009/0202516 A1 8/2009 Olmstead

FOREIGN PATENT DOCUMENTS

| WO | WO 2009/121183 A1 | 10/2009 |
|---|---|---|
| WO | WO 2011/098579 A1 | 8/2011 |

OTHER PUBLICATIONS

Whitchurch et al 2002( Science, 295' 1487).*
Eckhart et al. 2007. British Journal of Dermatology, 156(6): 1342-1345.*
Tetz et al. 2009. Antimicrobial Agents & Chemotherapy, 53(3): 1204-1209.*
Dapa et al., "Multiple Factors Modulate Biofilm Formation by the Anaerobic Pathogen *Clostridium difficile*," *J Bacteriol*. 195:545-555, 2013.
Dawson et al., "Characterization of *Clostridium difficile* Biofilm Formation, a Role for Spo0A," *PLoS One* 7:e50527, 2012.
Great Britain Search Report dated Sep. 12, 2012 for GB1208879.5 (4 pages).
Laning, "Characterization of the Clostridium Difficile Biofilm," *Master's Theses*, Paper 723, http://ecommons.luc.edu/luc_theses/723, 2012.
Rupnik et al., "*Clostridium difficile* Infection: New Developments in Epidemiology and Pathogenesis," *Nat Rev*. 7:526-536, 2009.

* cited by examiner

*Primary Examiner* — Padma V Baskar
(74) *Attorney, Agent, or Firm* — Klarquist Sparkman, LLP

(57) ABSTRACT

The invention relates to deoxyribonuclease for use in the treatment of a suspected or existing *C. difficile* infection; a pharmaceutical or veterinary composition or formulation comprising at least deoxyribonuclease for use in the treatment of a suspected or existing *C. difficile* infection; a combination therapeutic comprising at least deoxyribonuclease for use in the treatment of a suspected or existing *C. difficile* infection; a method of treating a mammal suspected of being infected with, or infected with, *C. difficile* comprising the use of at least deoxyribonuclease; a method of cleaning or sterilizing a material or product comprising the use of at least deoxyribonuclease; and a cleaning or sterilizing product impregnated with or containing at least deoxyribonuclease.

11 Claims, 16 Drawing Sheets

Figure 1:
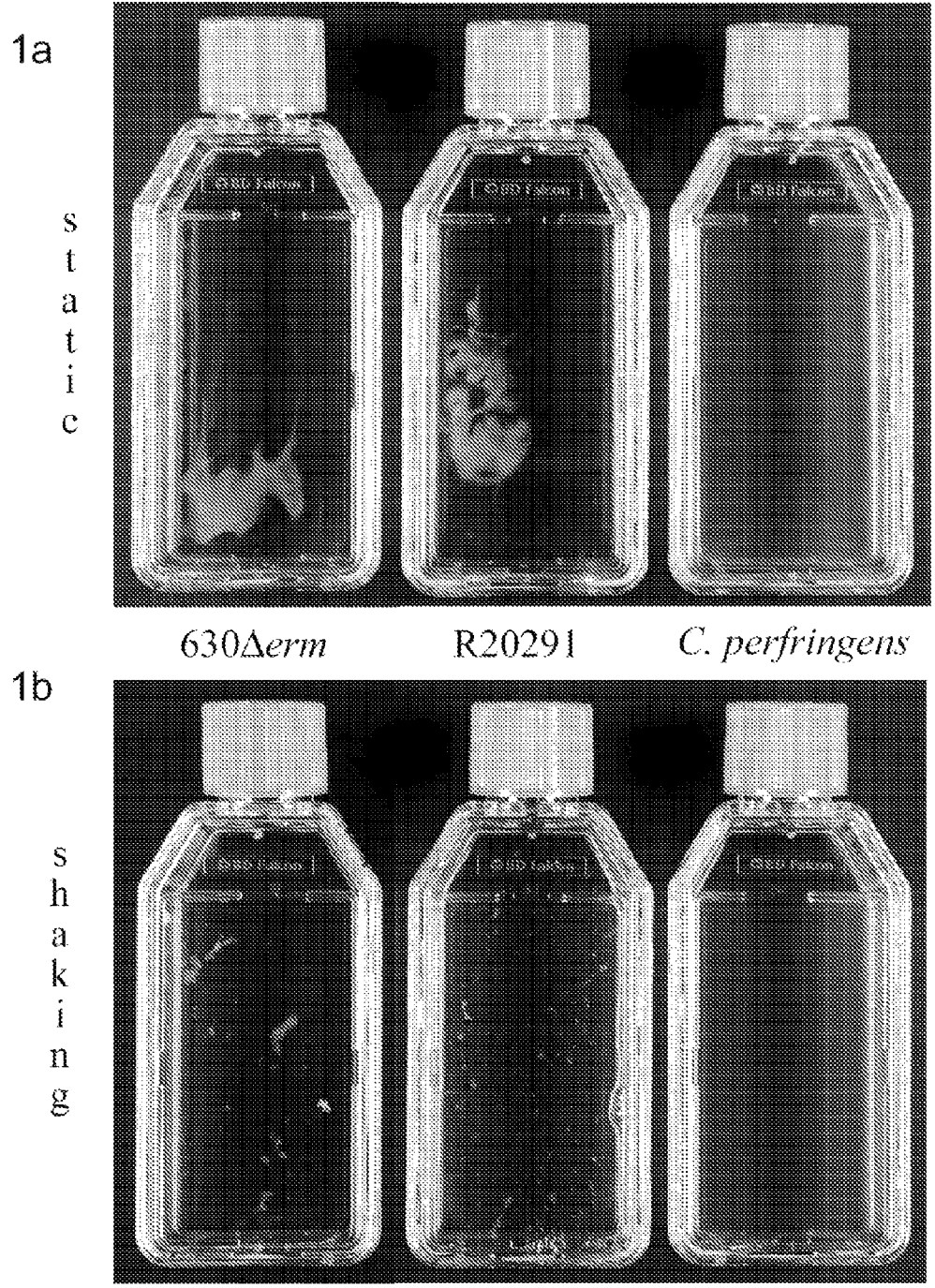

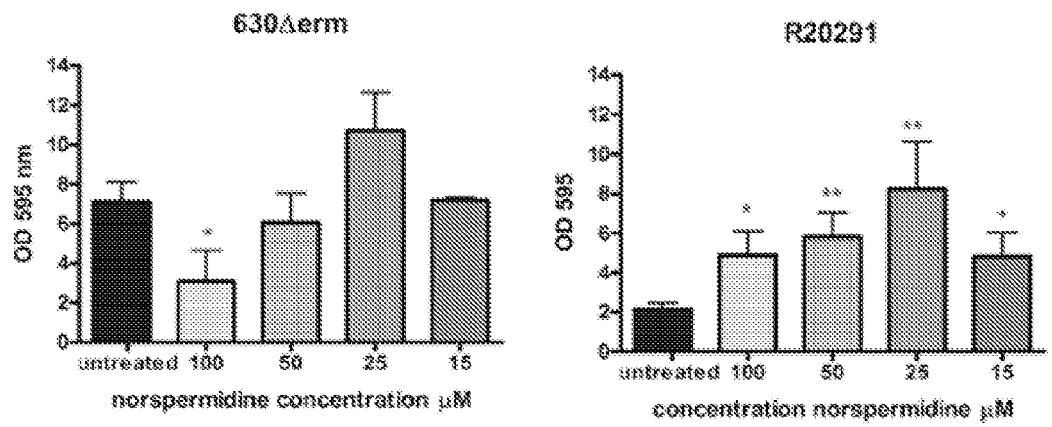
Figure 15
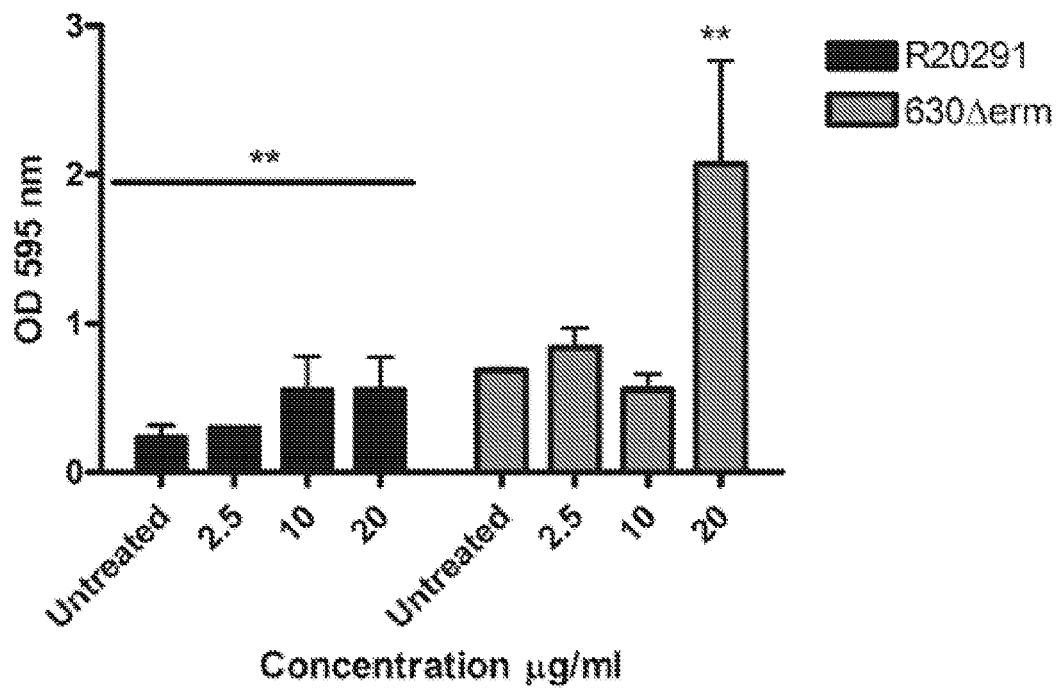

THERAPEUTIC FOR TREATING *CLOSTRIDIUM DIFFICILE* INFECTION

CROSS REFERENCE TO RELATED APPLICATIONS

This is the U.S. National Stage of International Application No. PCT/GB2013/051187, filed May 8, 2013, which was published in English under PCT Article 21(2), which in turn claims the benefit of United Kingdom Application No. 1208879.5, filed May 21, 2012.

FIELD OF THE INVENTION

The invention relates to deoxyribonuclease for use in the treatment of a suspected or existing *C. difficile* infection; a pharmaceutical or veterinary composition or formulation comprising at least deoxyribonuclease for use in the treatment of a suspected or existing *C. difficile* infection; a combination therapeutic comprising at least deoxyribonuclease for use in the treatment of a suspected or existing *C. difficile* infection; a method of treating a mammal suspected of being infected with, or infected with, *C. difficile* comprising the use of at least deoxyribonuclease; a method of cleaning or sterilising a material or product comprising the use of at least deoxyribonuclease; and a cleaning or sterilising product impregnated with or containing at least deoxyribonuclease.

BACKGROUND OF THE INVENTION

Healthcare-associated infections (HCAIs), or nosocomial infections, are those that are acquired by a patient during the course of receiving treatment within a healthcare setting. HCAIs can affect any part of the body, including the urinary system, the respiratory system, the skin, surgical wounds, the gastrointestinal system and even the bloodstream. Many such infections may arise from the presence of micro-organisms present on the body of the patient; however, they may also be caused by micro-organisms originating from another patient or from micro-organisms transmitted from the hospital environment due to poor hygiene.

HCAIs are amongst the major causes of death and increased morbidity in hospitalised patients. Each year, at least 2,000,000 patients in the USA and over 320,000 patients in the UK acquire one or more HCAIs during their stay in hospital. It is predicted that 1 in 4 patients in intensive care worldwide will acquire an infection during their treatment; this estimate is double in less developed countries. It has been reported that at any one time more than 1.4 million people worldwide are suffering from an HCAI. As a consequence, it is predicted patients spend an average of 2.5 times longer in hospital. In addition to a direct consequence on patient safety, HCAIs also constitute a significant financial burden on healthcare systems. In the USA, the risk of HCAIs has risen steadily over the last decade with accompanying costs estimated at US$ 4.5-5.7 billion a year. Similarly in the UK, HCAIs are estimated to cost the NHS £1 billion a year.

The micro-organisms giving rise to HCAIs are numerous, and may be in the form of any number of pathogens such as bacteria, virus, fungus, parasites or prions. The most commonly known nosocomial pathogens include methicillin-resistant *Staphylococcus aureus* (MRSA), *Clostridium difficile* (*C. difficile*) and *Escherichia coli* (*E. coli*).

*C. difficile* is a species of Gram-positive bacteria of the genus *Clostridium*. *C. difficile* is a commensal anaerobic bacterium of the human intestine present in approximately 2-5% of the population. However, an imbalance of gut bacterial load and infection with *C. difficile* can result is severe diarrhoea and intestinal dysfunction. The disease spectrum caused by *C. difficile* infection (CDI) ranges from mild self-limited illness to severe life-threatening conditions. Other example species of *Clostridium* causing human disease include *C. perfringens, C. tetani, C. botulinium, C. sordeffii* and *C. difficile*. Clostridial species are associated with diverse human diseases including tetanus, gas gangrene, botulism and pseudomembraneous colitis and can be a causative agent in food poisoning.

The pathogenesis of *C. difficile* has been attributed to various described putative virulence factors. The most widely described are the clostridial toxins designated toxin A (TcdA) and toxin B (TcdB), both of which are monoglucosyltransferases that are cytotoxic, enterotoxic, and pro-inflammatory. They belong to the large clostridial cytotoxin (LCT) family, and share approximately 66% amino acid homology with each other. The toxins are thought to target and inactivate the Rho-Rac family of GTPases in the host epithelial cells of the gut. This has been shown to result in actin depolymerisation by a mechanism correlated with a decrease in the ADP-ribosylation of the low molecular mass GTP-binding Rho proteins. This eventually results in massive fluid secretion, acute inflammation, and necrosis of the colonic mucosa.

*C. difficile* is identified as the most common cause of antibiotic associated diarrhoea. Since 2000, there has been a dramatic increase in the rates and severity of CDI particularly in North America and Europe. The primary risk factor for the development of CDI is the use of antibiotics disrupting the normal enteric bacterial flora enabling an overgrowth of ingested or endogenous *C. difficile*. However, the population at risk of suffering from CDI includes not only patients on antimicrobial and other therapies that can alter the balance of the gut flora, but also the immune-compromised (such as a consequence of disease or medical treatment) and the elderly. Other increased risk factors for CDI include length of hospital stay, use of feeding tubes, mechanical ventilation, invasive cannulae or catheters, and underlying co-morbidity. Accounts of relapse or re-infection of *C. difficile* in susceptible individuals is also documented with 15-35% of patients suffering relapse within the first 2 months post treatment.

Additionally, the incidence of CDI is further increased due to the sporulating nature of *C. difficile*. High levels of bacterial spores are present in hospital environments. Indeed, it has recently been shown that many standard hospital cleaning agents are ineffective at eradicating Clostridial spores from the environment, resulting in ineffective disease control.

The course of treatment of CDI can vary depending upon the stage and severity of the disease. For example, in early diagnosed or mild to moderate infections caused as a consequence of antibiotic administration, ceasing the treatment can re-establish the natural gut flora. However, in more severe cases, or recurring cases, vancomycin can be administered. Other treatment methods, particularly in the cases of multiple relapse, include re-establishment of the gut flora, for example, through use of probiotics such as *Saccharomyces boulardi* or *Lactobacillus acidophilus*, or by faecal bacteriotherapy (stool transplantation from an uninfected individual). However, two of the most difficult challenges for CDI treatment are the management of multiple recurrences and the management of fulminant or severe complicated CDI, in which cases if all existing treatment regimens fail, surgical removal of the colon can be the only remaining life-saving measure (Rupnik et al., 2009).

Prior to the production and release of toxinogenic compounds, the ingested spores of *C. difficile* remain dormant, forming non-reproductive structures in response to environmental stress. Once environmental conditions become favourable, the spores germinate and the bacteria proliferate into vegetative cells, which colonize the gastrointestinal (GI) tract of susceptible individuals. Bacterial spores, however, are extremely tolerant to many agents and environmental conditions including radiation, desiccation, temperature, starvation and chemical agents. This natural tolerance to chemical agents allows spores to persistent for many months in key environments such as hospitals or other healthcare centres.

Furthermore, many standard treatment methods, drugs, or antibacterial agents commonly used to treat bacterial infections have been associated with an increased risk of *C. difficile* colonisation and subsequent development of CDI. For example, typical antibacterial agents used to treat *Helicobacter pylori* infections are a combination of metronidazole, amoxicillin, levofloxacin or clarithromycin, all of which have strongly been associated with the development of CDI. Additionally, vancomycin used for the treatment of CDI is of concern due to its bacteriostatic action, relatively high cost and the possible development of resistance in *C. difficile* strains (and other bacteria). In fact, nearly every antibiotic has been associated with subsequent CDI, but some carry a higher risk than others (Rupnik et al., 2009). Current therapies are therefore extremely limited in the treatment or control of *C. difficile* related infections particularly in view of the fact nearly all antibiotic classes are associated with causing or exacerbating the disease.

Consequently, there is an increasing need to develop new and efficacious agents or treatment regimens to reduce the incidence and likelihood of suffering from CDI, and other similar diseases associated with spore forming bacteria. Many existing therapies to treat or reduce the incidence of CDI and *C. difficile* spread either attempt to re-establish the native gut microorganism population, reduce the levels of *C. difficile* toxins or stimulate the immune system.

The exact mechanism by which colonization of the gut by *C. difficile* occurs, and therefore how the organism establishes itself in the gut to lead to CDI, remains unclear. Colonisation is thought to enable the organism to penetrate the mucus layer and attach to the underlying colonic epithelial cells, thereby facilitating the delivery of toxins to host cell receptors. Surface attachment is a property of many bacterial species, which permits colonization of specific niches. For many pathogenic bacteria, formation of biofilms (containing an extracellular polymeric substance EPS matrix) is linked to colonization, maintenance and disease. Biofilms are defined as polymicrobial aggregates attached to each other and/or to surfaces. These aggregates are referred to by several terms; films, mats, flocs, sludge or biofilms. Many pathogenic bacteria form biofilms in response to a diverse array of environmental cues, for self-preservation, evasion of the host immune response, mechanical integrity and preservation of nutrients, or colonization of a particular niche. As well as providing a protective environment from external influences such as, host immune response, desiccation, biocides and some antibiotics, biofilms can also provide a nutrient source and promotes recycling of lysed cells. It has been shown that bacterial surface structures such as flagella, pili and fimbriae can stabilize the biofilm.

In some species the extracellular polymeric substance (EPS) matrix accounts for as much as 90% of the biofilm biomass, with the remainder comprising bacteria. The EPS matrix provides the scaffold by which bacteria adhere to each other and to surfaces. The composition and architecture of the EPS is species and even strain dependent but the majority are comprised of polysaccharides, nucleic acids, lipids and proteins, which are secreted by biofilm producing bacteria. Furthermore, the composition of an EPS can vary greatly between biofilms of the same species and is influenced by many factors, including the microorganisms present, the shear forces experienced, the temperature and the availability of nutrients. The identification of a biofilm and its components depends on the isolation and culture methods used, particularly as the composition can vary, and therefore different experimental methods are required to isolate different biofilms. Consequently, the nature and identification of biofilms has to be specific for each type of biofilm under investigation.

Currently, there exists uncertainty as to whether *Clostridium* species, and in particular *C. difficile*, produces a biofilm. Biofilms have been found to be involved in a wide variety of microbial infections in the body, it has been suggested that they are involved in 80% of all infections, with common examples including urinary tract infections, catheter infections, middle-ear infections, formation of dental plaque, endocarditis, and infections symptomatic of cystic fibrosis. Given these facts, researchers consider *C. difficile* may produce a biofilm to promote colonisation. However, reports in the art are conflicting since Reynolds et al, 2010 state *C. difficile* does not exhibit biofilm formation, whereas Shirtliff et al 2012 believe it does (http://www.dental.umaryland.edu/dentaldepts/micropath/shirtliff_lab_projects_clostridium-.html).

Therefore, it is generally acknowledged that is unknown to what extent, if any, adhesion and biofilm production are involved in the pathogenesis of *C. difficile* (Rupnik et al., 2009).

However, our investigations have revealed conclusive evidence that a variety of clinical isolates of *C. difficile* form biofilms, in both rich and non-rich media. Furthermore, we have shown for the first time that that both the super-structure and sub-structures of these biofilms differ depending on environmental conditions, such as nutrient availability and growth parameters. This hitherto unknown characteristic may contribute to the pathogenicity of the bacteria, providing protection against immune responses, and permitting adhesion and colonisation of the gut leading to infection. Furthermore, uniquely, we have found that the biofilms comprise a substantial number of live bacteria, which may serve to provide a reservoir of *C. difficile* for re-colonising the host following treatment and so may account for the significant relapse incidence associated with *C. difficile* infection.

Moreover, our further analysis of the *C. difficile* biofilm revealed its primary component is nucleic acid which we discovered, upon treatment with deoxyribonuclease, is degraded effectively in a dose dependent manner. Additionally, we also discovered that pre-treatment of bacterial culture vessels with deoxyribonuclease inhibited the formation of a *C. difficile* biofilm. Therefore, the use of deoxyribonuclease against CDI represents a potential new avenue for therapeutic intervention in the treatment of CDI, potentially reducing the pathogenicity of the bacteria and its ability to colonise the host, in addition to increasing its susceptibility to host immune defence mechanisms and sensitivity to other existing antibacterial agents. Consequently, this has important implications in treating CDI, reducing the incidence of disease spread, and relieving the burden currently shouldered by healthcare organisations.

STATEMENTS OF INVENTION

According to a first aspect of the invention, there is provided deoxyribonuclease, or a functional fragment thereof, for use in the treatment of *C. difficile* infection (CDI).

As will be appreciated by those skilled in the art, reference herein to "C. difficile infection" refers to a suspected or a diagnosed infection and so to instances where the CDI is either asymptomatic or symptomatic and in the latter case characteristic of the abnormal colonization of the gut by the C. difficile bacterium where the increase in C. difficile bacterial load is above that normally found in the body and which, if left untreated, would result in advancing signs and/or symptoms indicative of the diseased or pathological state.

Reference herein to "deoxyribonuclease' refers to any enzyme that catalyzes the hydrolytic cleavage of phosphodiester linkages in the DNA backbone.

In a preferred embodiment of the invention, ideally said deoxyribonuclease is selected from the group comprising: DNase I; DNase II; DNase III; DNase IV; or LS DNase.

Yet more ideally, said deoxyribonuclease is selected from the group comprising: DNase I; or DNase II. Most ideally, said deoxyribonuclease is DNase I.

Reference herein to a functional fragment of deoxyribonuclease, refers to a functional fragment, or part, of a deoxyribonuclease enzyme that catalyzes the hydrolytic cleavage of phosphodiester linkages in the DNA backbone and so is a region of said deoxyribonuclease protein that retains catalytic activity. Thus it includes truncated, but functional versions, of the enzyme and/or variants and/or derivatives and/or homologues whose functionality is maintained.

In a further preferred embodiment of the invention, said fragment of deoxyribonuclease comprises, at least, the catalytic unit of the deoxyribonuclease enzyme.

As will be appreciated by those skilled in the art homologues or derivatives of deoxyribonuclease, and the different variants thereof, will also find use in the context of the present invention. Thus, for instance deoxyribonucleases which include one or more amino acid additions, deletions, substitutions or the like are encompassed by the present invention. Those skilled in the art will appreciate similar modifications can be made to these ideal structures to achieve the same effect providing enzymatic functionality is retained.

In yet a further preferred embodiment of the invention, said deoxyribonuclease is mammalian deoxyribonuclease such as, but not limited to, human, bovine, porcine, ovine, feline, canine, equine, ungulate or the like. More ideally, said deoxyribonuclease is selected from the group comprising: bovine deoxyribonuclease; human deoxyribonuclease, or recombinant versions thereof. Most ideally, said deoxyribonuclease is human, or a recombinant version thereof.

In yet a further preferred embodiment of the invention, said deoxyribonuclease is a recombinant molecule.

In yet a further preferred embodiment of the invention, said deoxyribonuclease degrades C. difficile biofilm. As will be appreciated by those skilled in the art, this will potentially reduce the pathogenicity of the bacteria impairing its ability to colonize the host gut, thereby preventing, reducing and/or eradicating infection by the bacteria.

In yet a further preferred embodiment of the invention, the concentration of said deoxyribonuclease is, without limitation, between 1-1000 µg/ml and ideally between 100-1000 µg/ml, most ideally between 250-1000 µg/ml including all 1 µg/ml integers there between. At these concentrations we have found that C. difficile biofilm is degraded and/or prevented from forming. Moreover, we have found that the effectiveness of the deoxyribonuclease is increased or decreased in a dose dependent manner. However, as will be appreciated by those skilled in the art, the concentration of deoxyribonuclease will vary according to the specific nature of the deoxyribonuclease used, with different deoxyribonucleases known to have different relative enzymatic activity. In certain instances 1-10 mg are given to a patient daily, ideally 2-8 mg and more ideally still 2.5 mg, 5 mg or 7.5 mg, although 2.5 mg is preferred.

In a preferred embodiment of the invention said deoxyribonuclease is used in combination with, either sequentially or simultaneously, a proteinase such as Proteinase K.

According to a second aspect of the invention there is provided the use of a deoxyribonuclease in the manufacture of a medicament to treat a C. difficile infection.

According to a third aspect of the invention there is provided a pharmaceutical composition or a pharmaceutical formulation comprising deoxyribonuclease according to any of the above aspects or embodiments of the invention in combination with a suitable carrier.

Preferably said composition is formulated for medical or veterinary use.

The carrier, or, if more than one is present, each of the carriers, must be acceptable in the sense of being compatible with the other ingredients of the formulation and not deleterious to the recipient.

The formulation includes those suitable for rectal, oral, nasal, bronchial (inhaled), topical (including eye drops, buccal and sublingual), vaginal or parenteral (including subcutaneous, intramuscular, intraperitoneal, intravenous and intradermal) administration and may be prepared by any methods well known in the art of pharmacy.

The route of administration will depend upon the condition to be treated but preferred compositions are formulated for rectal, intravenous, parenteral, oral, nasal, bronchial or topical administration.

The composition may be prepared by bringing into association the deoxyribonuclease of the invention and the carrier. In general, the formulations are prepared by uniformly and intimately bringing into association the deoxyribonuclease with liquid carriers or finely divided solid carriers or both, and then if necessary shaping the product. The invention extends to methods for preparing a pharmaceutical composition comprising bringing a deoxyribonuclease of the invention in association with a pharmaceutically or veterinarily acceptable carrier or vehicle.

Formulations for oral administration in the present invention may be presented as: discrete units such as capsules, sachets or tablets each containing a predetermined amount of deoxyribonuclease; as a powder or granules; as a solution or a suspension of the active conjugate in an aqueous liquid or a non-aqueous liquid; or as an oil-in-water liquid emulsion or a water in oil liquid emulsion; or as a bolus, or the like.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the deoxyribonuclease in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored.

Other formulations suitable for oral administration include lozenges comprising deoxyribonuclease in a flavoured base, usually sucrose and acacia or tragacanth; pastilles comprising deoxyribonuclease in an inert base such as gelatin and glycerin, or sucrose and acacia; and mouthwashes comprising deoxyribonuclease in a suitable liquid carrier.

For topical application to the skin, deoxyribonuclease may be made up into a cream, ointment, jelly, solution or suspension, or the like. Cream or ointment formulations that may be used for the conjugate are conventional formulations well known in the art, for example, as described in standard text books of pharmaceutics such as the British Pharmacopoeia.

According to a yet further aspect of the invention there is provided a combination therapeutic comprising the above described deoxyribonuclease therapeutic, in any aspect or embodiment thereof, in combination with at least one other therapeutic.

We have found that deoxyribonuclease degrades biofilm formation in *C. difficile*. Consequently, as will be appreciated by those skilled in the art, its use in combination with other agents such as, but not limited to, antibiotics, antibody therapeutics or other like cytotoxic agents, will improve the relative efficacy of the deoxyribonuclease therapeutic against *C. difficile*. In a preferred embodiment of the invention said deoxyribonuclease is used in combination with, either sequentially or simultaneously, a proteinase such as Proteinase K.

According to yet a further aspect of the invention there is provided a method of treating a mammal suffering from a *C. difficile* infection comprising administering to said mammal an effective amount of said deoxyribonuclease, therapeutic or composition of the invention.

In a preferred embodiment of the invention, said mammal is a primate. More ideally, said mammal is human, equine, canine, feline, porcine, ovine, ungulate or any other domestic or agricultural species. Yet most ideally, said mammal is human. In a preferred embodiment of the invention said deoxyribonuclease is used in combination with, either sequentially or simultaneously, a proteinase such as Proteinase K.

According to yet a further aspect of the invention, there is provided a method of cleaning or sterilising a material susceptible to colonisation by, or colonised with, *C. difficile* comprising applying to said material a deoxyribonuclease enzyme, or a functional fragment thereof.

In a preferred embodiment of this method, preferably said material is a plastics material. In a preferred embodiment of the invention said deoxyribonuclease is used in combination with, either sequentially or simultaneously, a proteinase such as Proteinase K.

We have advantageously shown that pre-treatment of materials with DNase reduces the ability of *C. difficile* to produce a biofilm. Consequently, as will be appreciated by those skilled in the art, deoxyribonuclease enzyme can advantageously be used to breakdown *C. difficile* biofilms and so aid the sterilisation of materials, such as but not limited medical devices, hospital equipment, equipment used in the preparation of food, or any such like materials where there is a risk of contamination with the bacterium *C. difficile*.

According to a further embodiment of the invention there is provided a cleaning or sterilising product comprising at least deoxyribonuclease and a suitable carrier.

Preferably said product comprises at least one other cleaning agent such as, but not limited to, a detergent or an abrasive agent. More preferably still, said product is in the form of a liquid. Yet more preferably still, said product is in the form of a wipe or cleaning cloth impregnated with or containing at least said deoxyribonuclease and, optionally, a suitable carrier. In a preferred embodiment of the invention said product also comprises a proteinase such as Proteinase K.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 2:
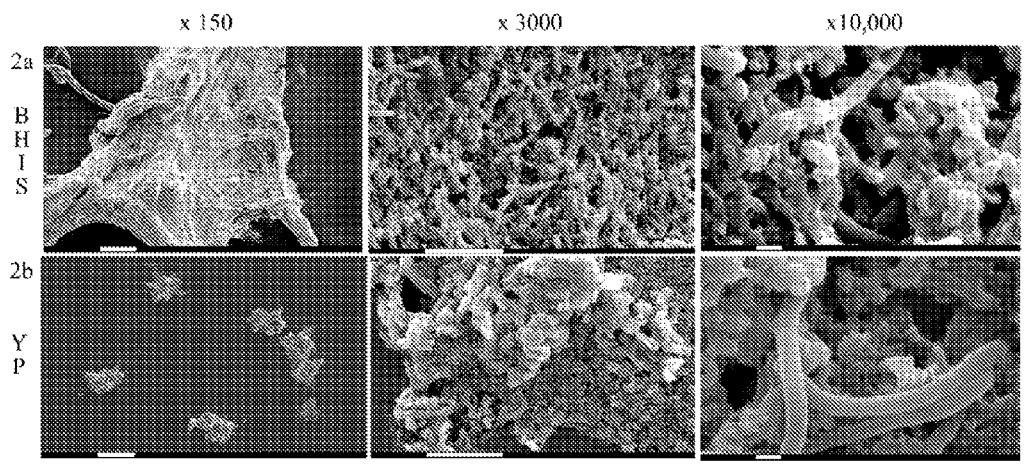
Figure 3:
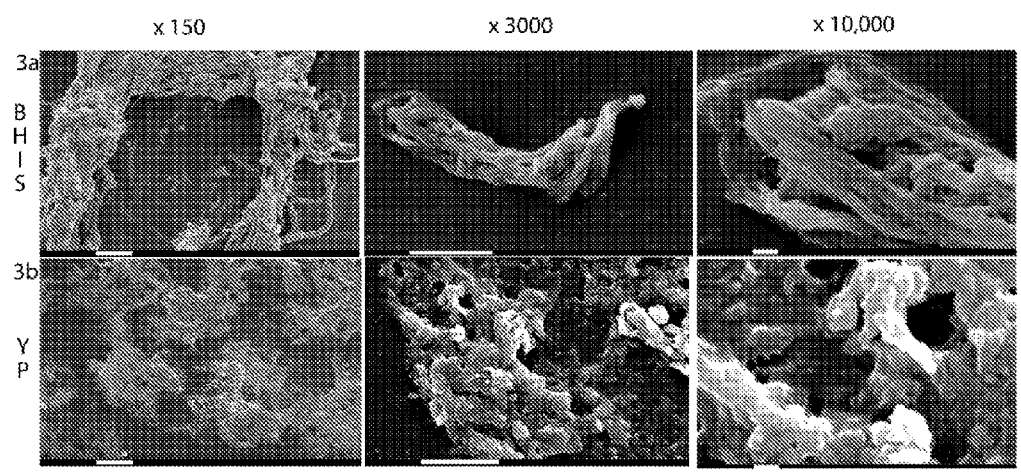
Figure 4:
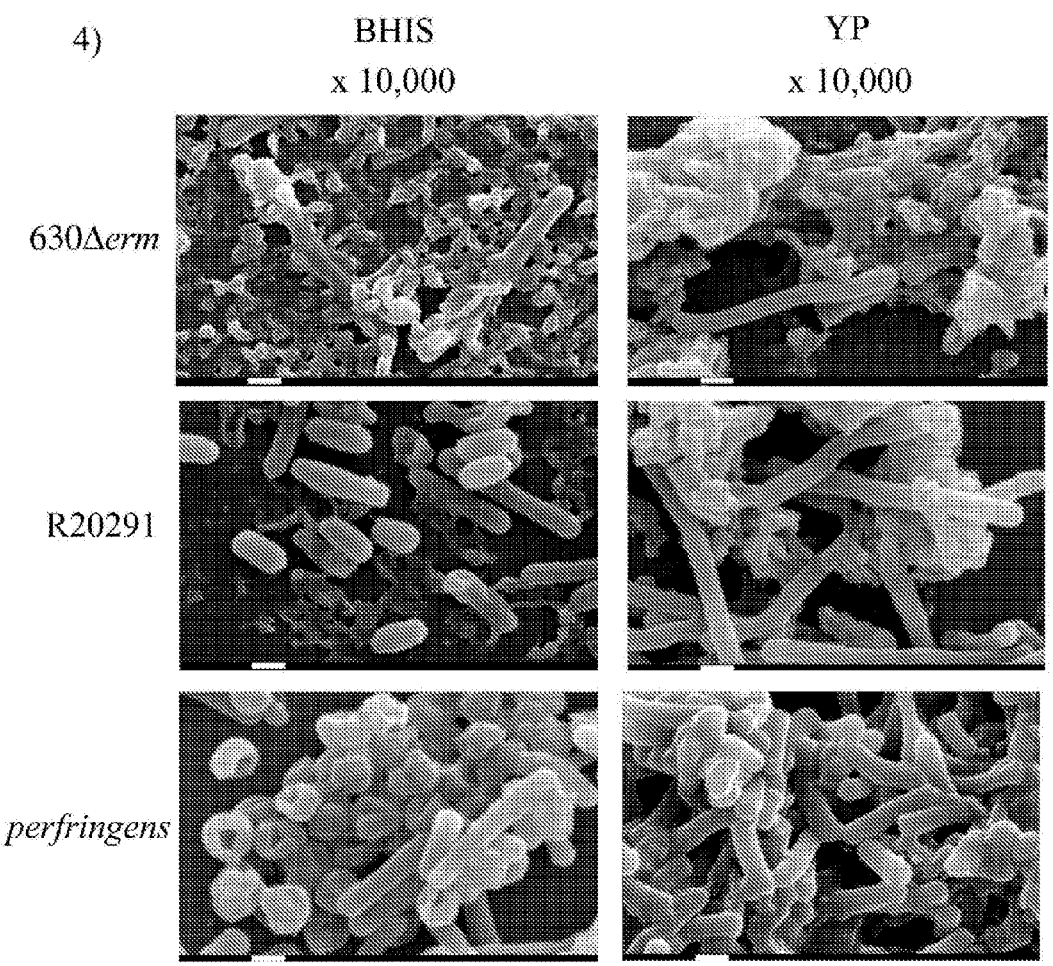
Figure 5:
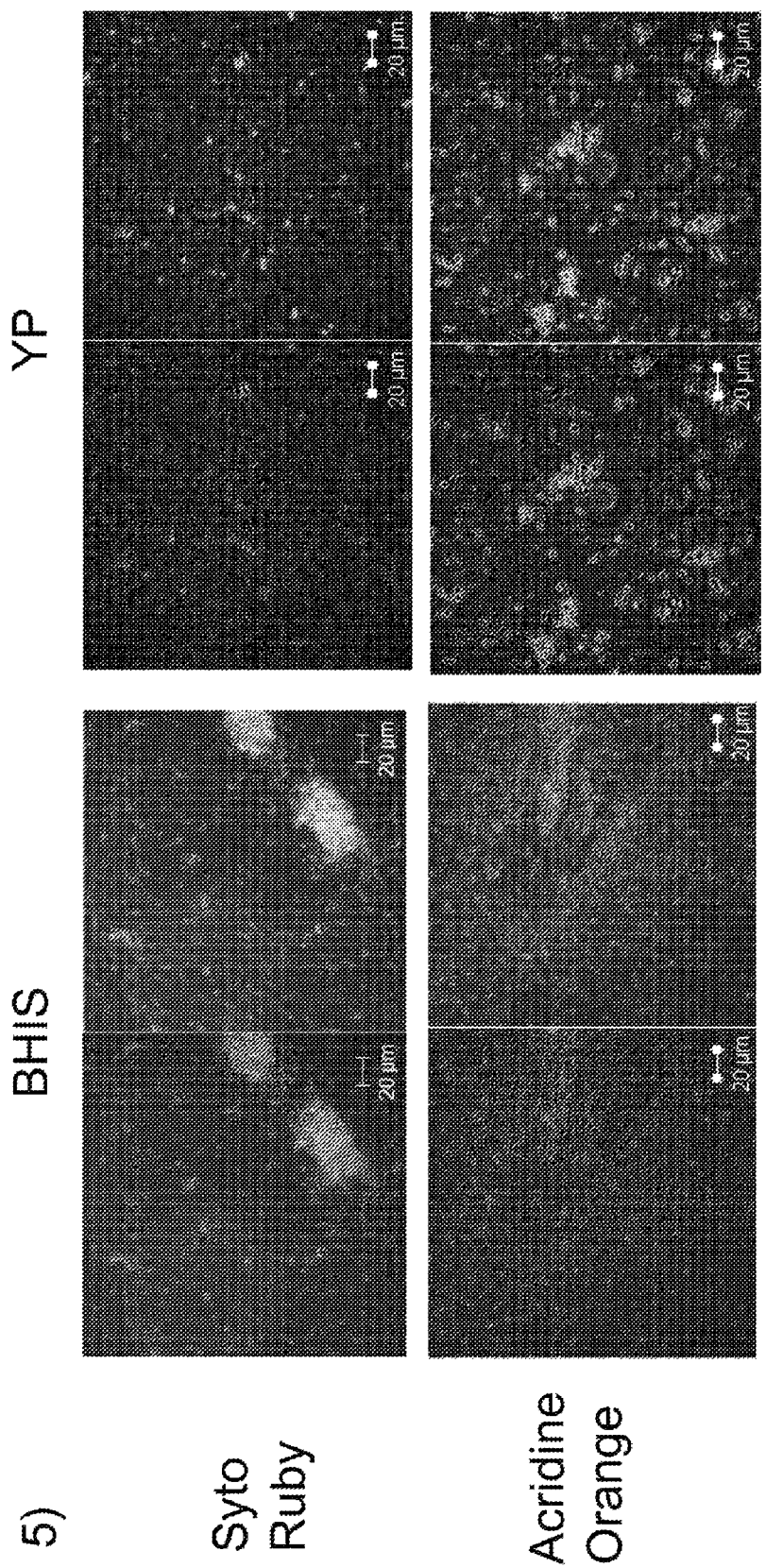
Figure 6:
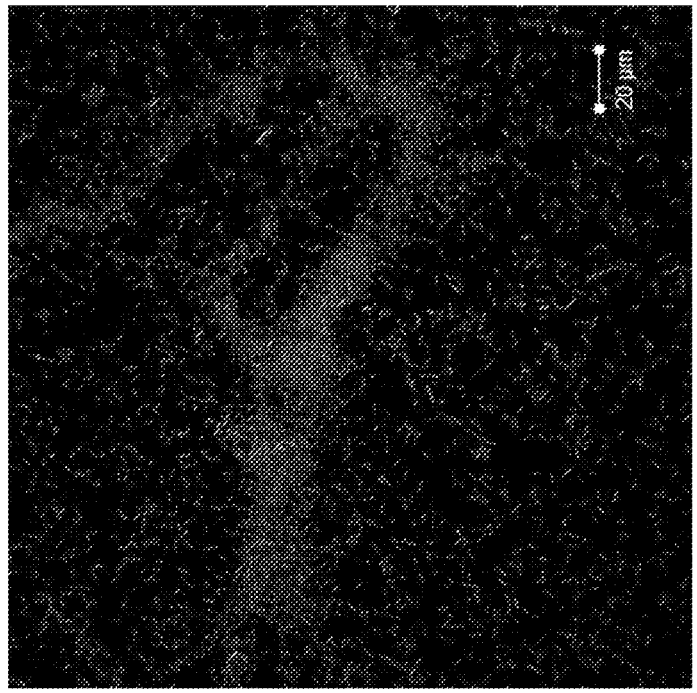
Figure 7:
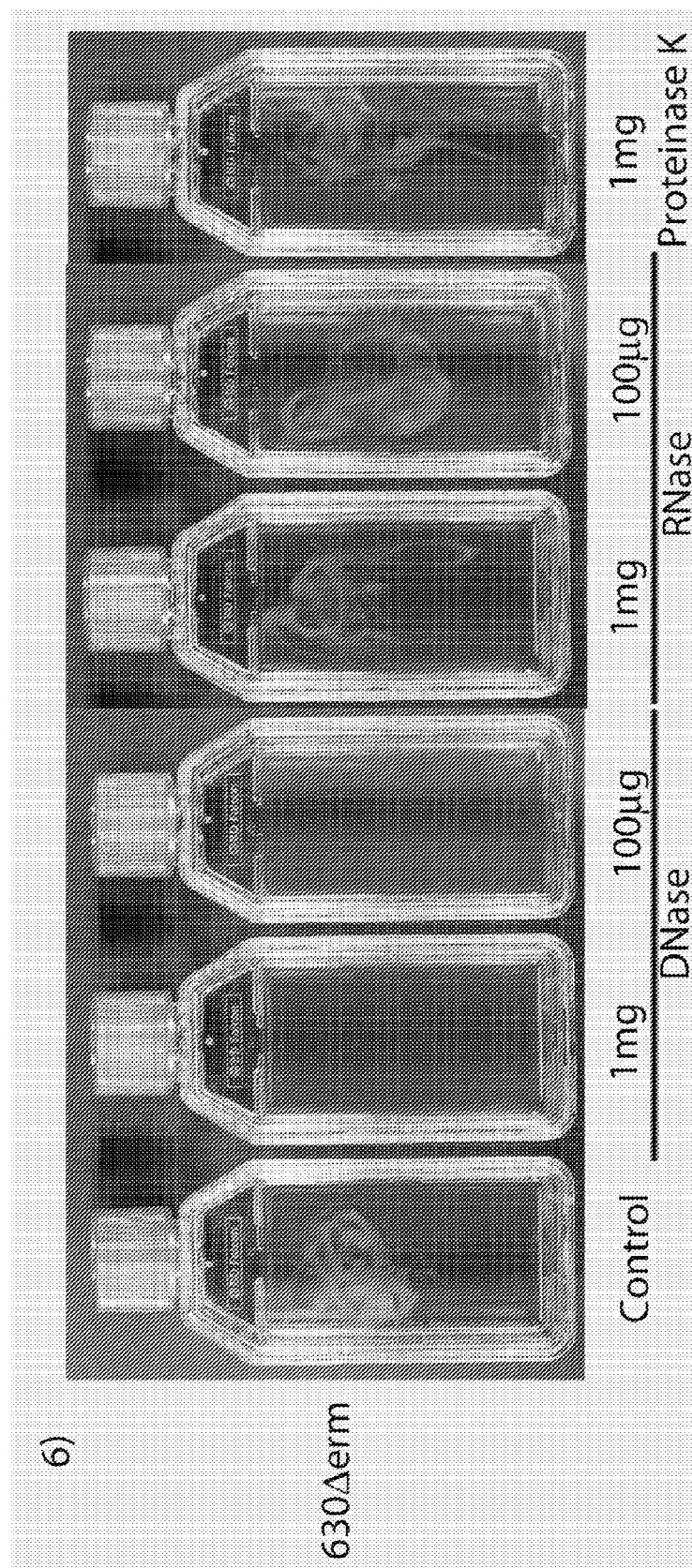
Figure 8:
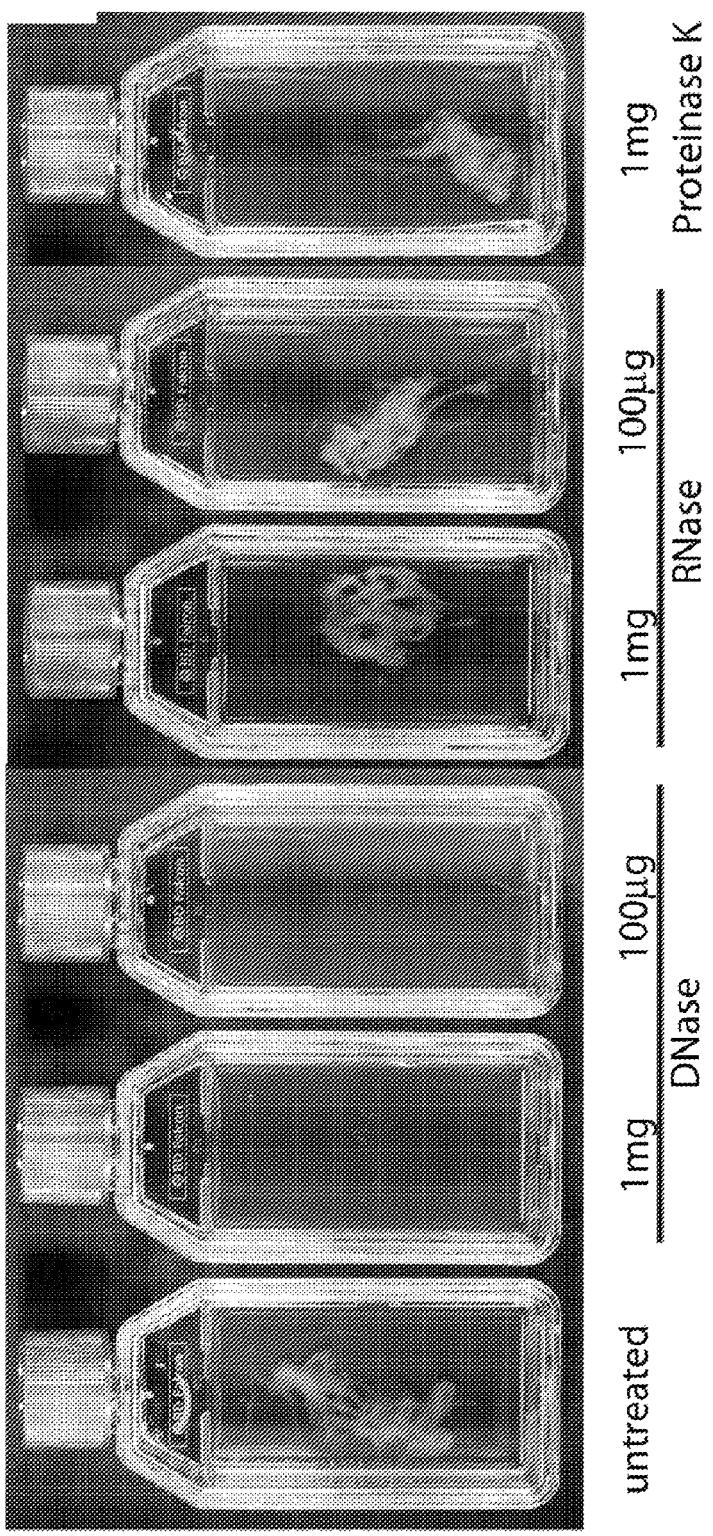
Figure 9:
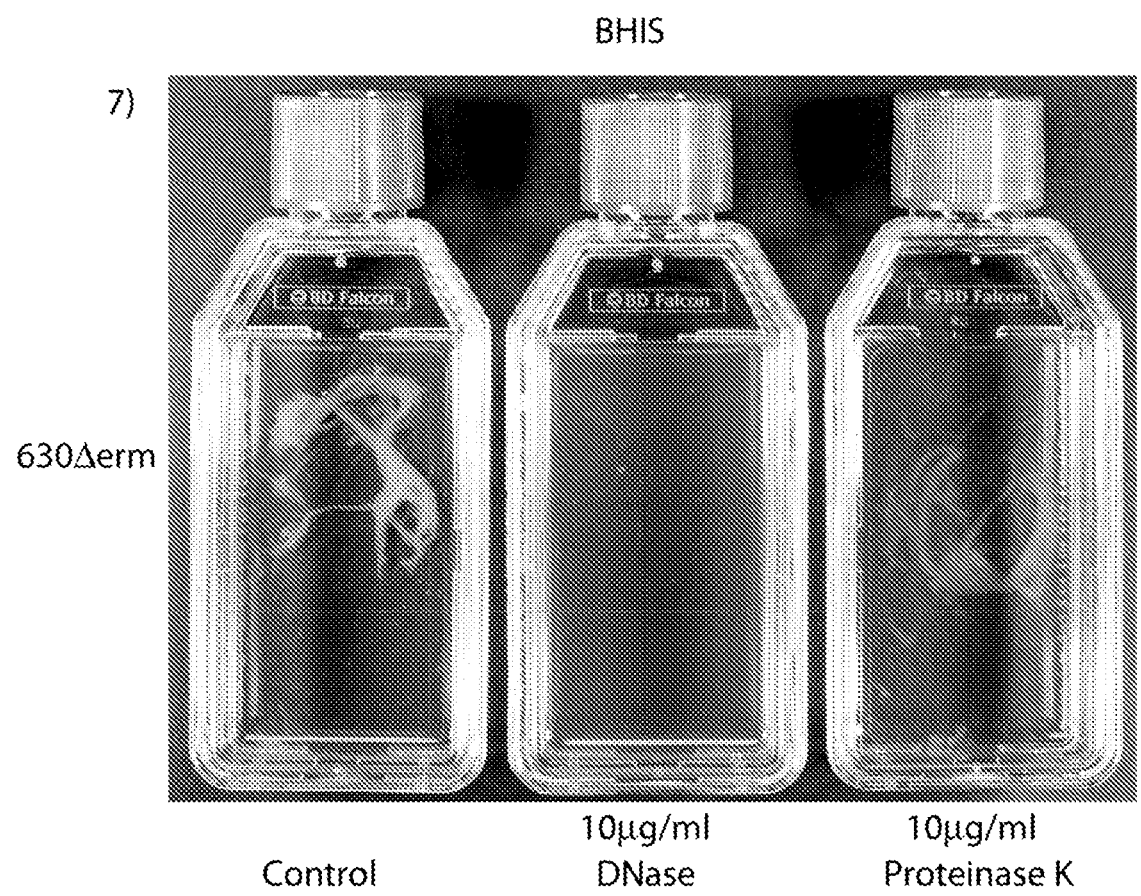
Figure 10:
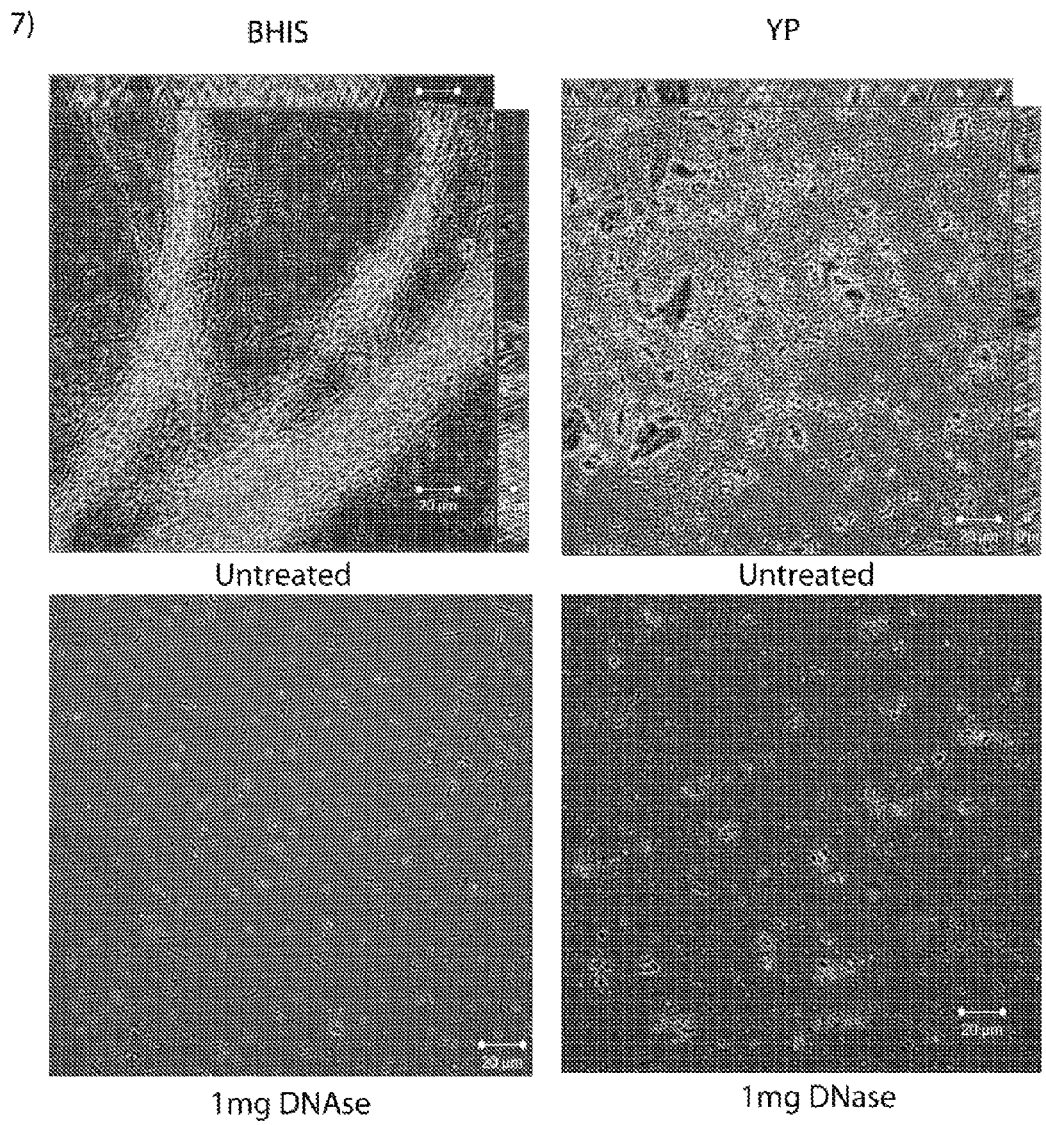
Figure 11:
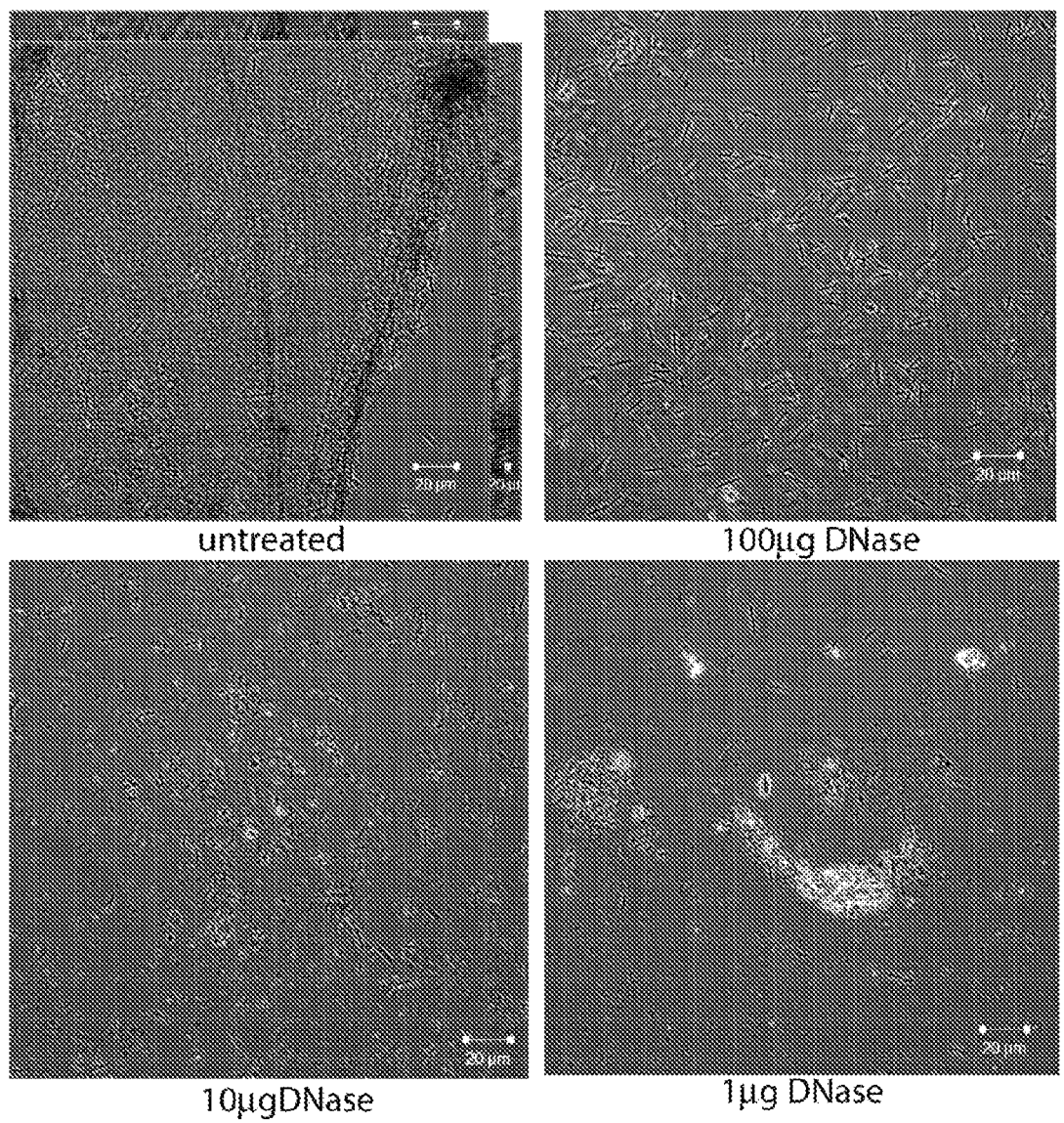
Figure 12:
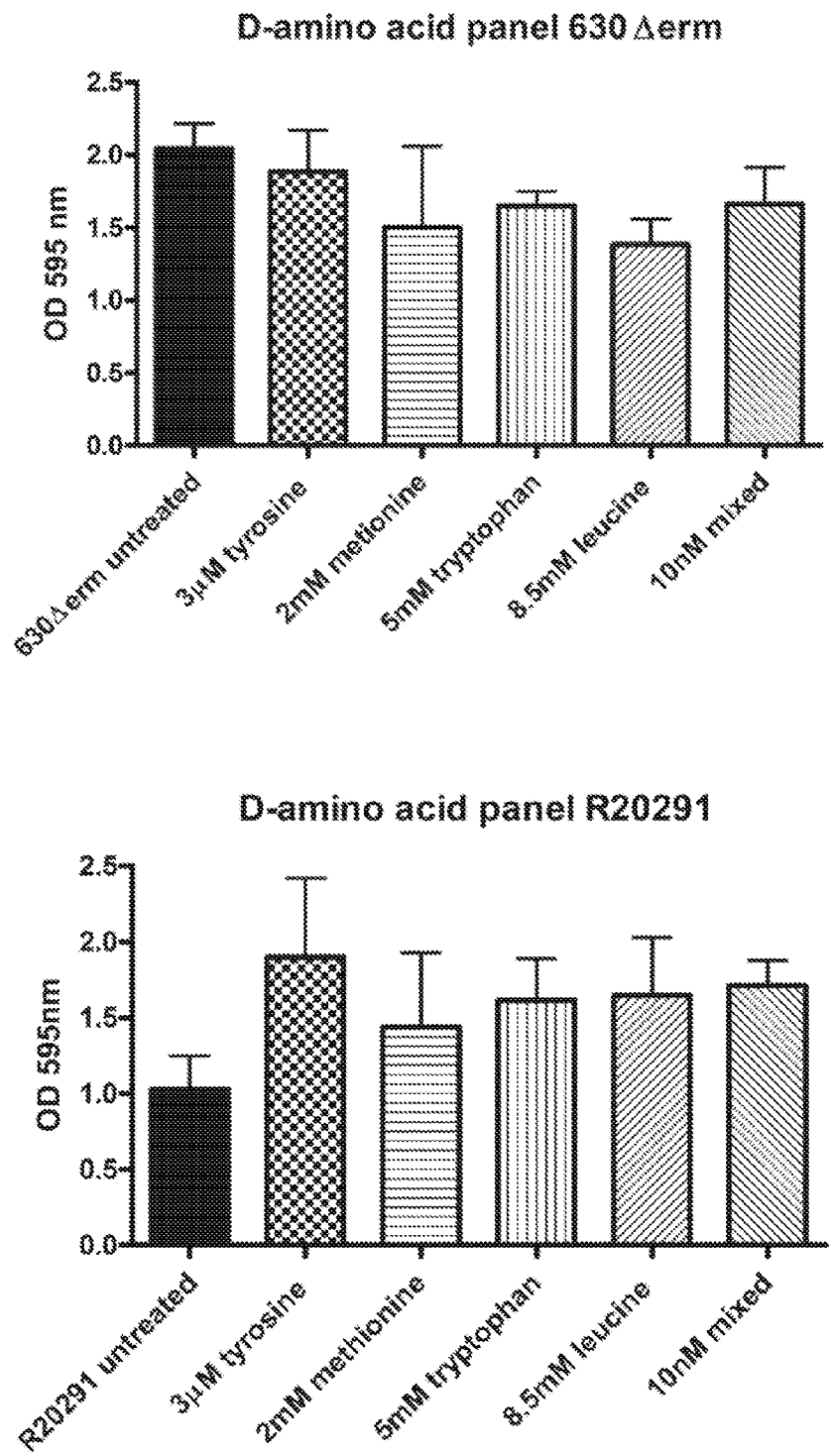

The present invention will now be described by way of example only with particular reference to the following figures wherein:

FIG. 1. Biofilm formation in cultures of different strains of *Clostridium* bacteria. Bacterial strains were grown under static or shaking conditions in rich liquid media (BHIS), with biofilms observed in cultures of both strains of *C. difficile* (630Δerm and R20291) but not *C. perfringens*. The appearance of the biofilms formed by the *C. difficile* isolates differed under static or agitated culture (FIGS. 1*a* & *b*);

FIG. 2. SEM analysis of 630Δerm *C. difficile* biofilm formed in static culture. Biofilms formed in rich liquid media (BHIS) and non-rich liquid media (YP) under static culture conditions as shown by SEM. Biofilms in rich media are denser than the aggregates observed in YP media, with visible bacterial-matrix connections;

FIG. 3. SEM analysis of 630Δerm *C. difficile* biofilm formed in agitated culture. Biofilms formed in rich liquid media (BHIS) and non-rich liquid media (YP) under agitated culture conditions as shown by SEM. Biofilms in rich media are denser than the aggregates observed in YP media, but there are no visible bacterial-matrix connections with bacteria occluded by the biofilm matrix;

FIG. 4. SEM analysis of different *Clostridium* bacteria cultured on glass coverslips in rich (BHIS) or non-rich (YP) media. Bacteria adhere most effectively to the plastic compared to the glass, with bacteria-matrix connections dependent upon bacterial strain and media. Observed bacilli were longer for 630Δerm and R20291 in YP media compared to those BHIS media, with multifarious matrix connections. Spores were only observed in BHIS culture;

FIG. 5. Confocal microscopy of 630Δerm *C. difficile* biofilm cultured in rich (BHIS) and non-rich (YP) media revealed *C. difficile* biofilms are composed of both nucleic acid and protein. Slides were stained with acridine orange (nucleic acid stain) and SYPRO Ruby (Protein stain). Both protein and nucleic acid are present in the biofilms, with a greater abundance of nucleic acid observed in both culture media;

FIG. 6. *C. difficile* biofilms are mainly comprised of live bacterial cells. Confocal microscopy of 630Δerm and R20291 *C. difficile* biofilms cultured in rich (BHIS) media stained with syto9, which stains live cells green and propidium iodide which stains dead or dying cells red. The majority of bacteria appear as green and so are viable;

FIG. 7. Biofilm produced by 630Δerm can be degraded with DNase, but not RNase or proteinase K. Cultures containing biofilm were treated with DNase, RNase or proteinase K for 15 minutes at the concentrations indicated. Biofilm was only degraded by DNase treatment;

FIG. 8. Biofilm produced by R20291 strain can be degraded with DNase, but not RNase or proteinase K. Cultures containing biofilm were treated with DNase, RNase or proteinase K for 15 minutes at the concentrations indicated. Biofilm was only degraded by DNase treatment;

FIG. 9. DNase inhibits formation of biofilms in liquid media. Addition of DNase (10 mg/ml) into the growth media inhibits the formation of biofilm for *C. difficile* strain 630Δerm. Proteinase K (10 mg/ml) supplementation in the growth media, decreases biofilm formation in *C. difficile* strain 630Δerm, compared to the untreated control. All samples were incubated statically for six days;

FIG. 10. Confocal microscopy of 630Δerm *C. difficile* biofilms treated with DNase. Upon treatment of *C. difficile* biofilms with DNase the biofilm is degraded in a dose-dependent manner;

FIG. 11. Confocal microscopy of 630Δerm *C. difficile* biofilms treated with varying concentrations of DNase. The degradation of the *C. difficile* biofilm was dose dependent, with incomplete digestion observed at 10 ug and more notably 1 ug DNase;

FIG. 12. Disassembly of biofilms was investigated. In *B. subtilis*, certain D-amino acids and norspermidine have been shown to disassemble biofilms. These D-amino acids also prevented biofilm formation in *E. coli* and *S. aureus* and *P. aeruginosa*. A range of concentrations of the D-amino acids known to be effective against other bacteria were used.

In *B. subtilis* biofilms have been disassembled with: 3 μM D-tyrosine, 2 mM D-methionine, 5 mM D-tryptophan, 8.5 mM D-leucine, and then a mixture of each, (2.5 nM each D-amino acid above). In *S. aureus* films have been disassembled with 10 μM, 100 μM and 500 μM D-phenylalanine, D-proline and D-tyrosine.

However, no significant effect was observed against *C. difficile* strains (upper) 630Δerm and (lower) R20291 when using 3 μM D-tyrosine, 2 mM D-methionine, 5 mM D-tryptophan, 8.5 mM D-leucine, and then a mixture of each, (2.5 nM each D-amino acid above).

The graphs show that *C. difficile* biofilms are not disrupted by D-amino acids when tested in the same way the *B. subtilis* biofilms are disassembled.

Figure 13:
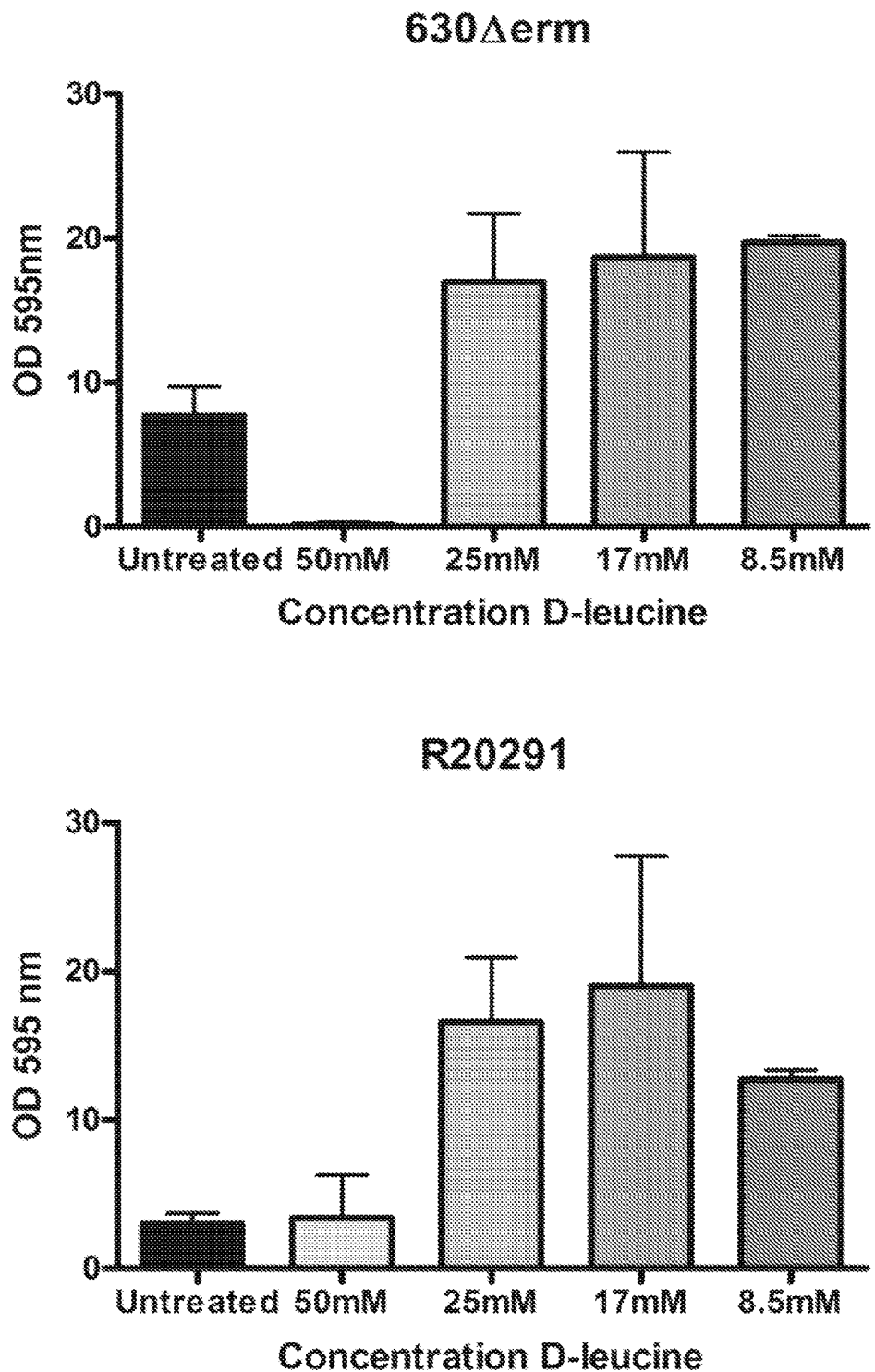

FIG. 13. Shows the effect of D-leucine on biofilm formation in *C. difficile* strains (upper) 630Δerm and (lower) R20291. Unfortunately, the growth of 630Δerm is inhibited in 50 mM D-leucine and reduced in R20291. Therefore we are not seeing biofilm disassembly at 50 mM, as there is no growth of the bacteria in strain 630Δerm to form a biofilm. At lower concentrations the amino acid appeared ineffective.

Figure 14:
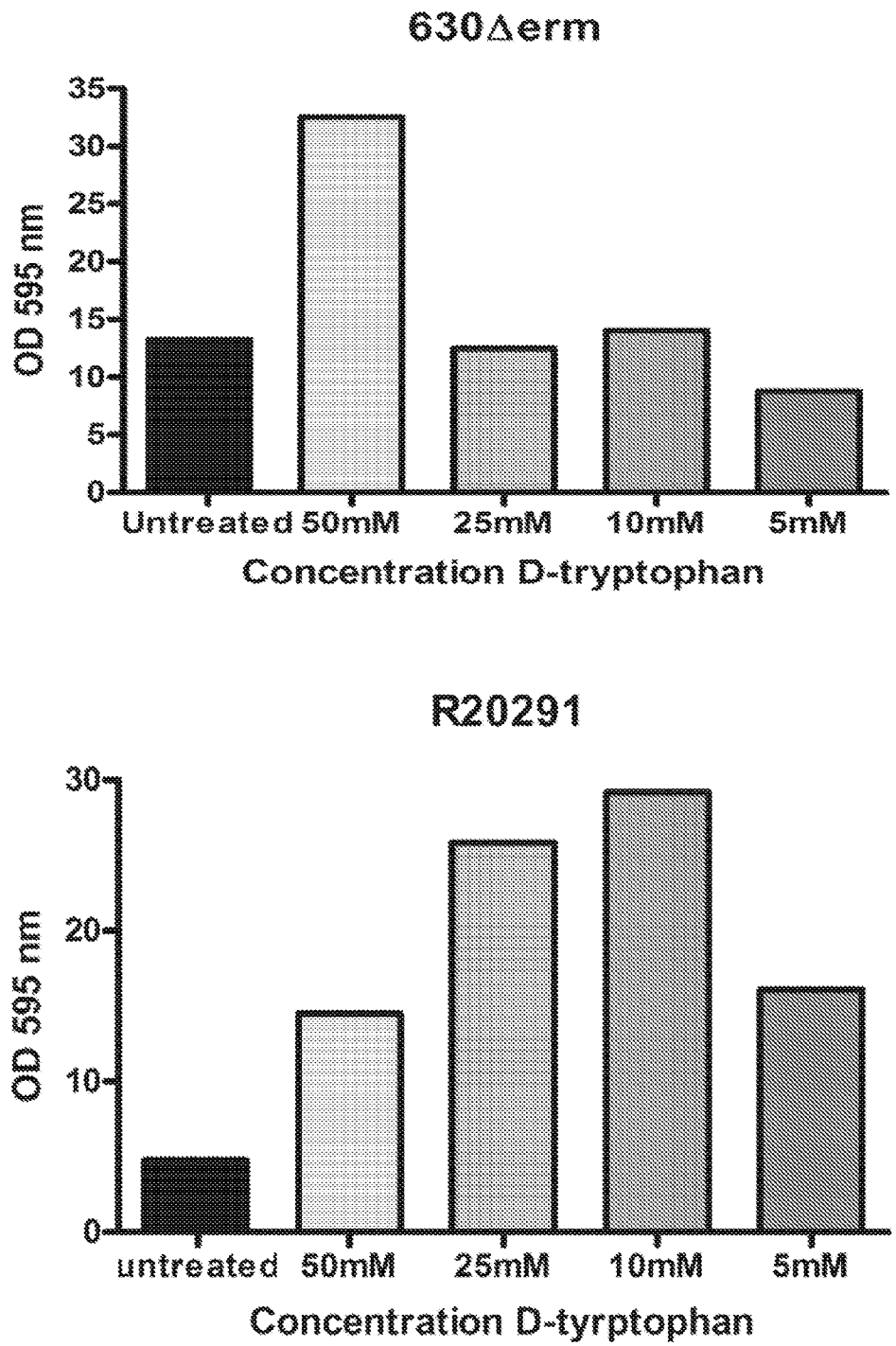

FIG. 14. Shows the effect of D-tryptophan on biofilm formation in *C. difficile* strains (upper) 630Δerm and (lower) R20291. The graphs show that *C. difficile* biofilms are not disrupted by D-tryptophan.

FIG. 15. Shows the effect of norspermidine on biofilm formation in *C. difficile* strains (upper) 630Δerm and (lower) R20291. Norspermidine has been shown to disassemble biofilms in *B. subtilis* at 100, 50 and 25 μM. From the graphs it is clear that norspermidine does not disassemble biofilms in *C. difficile* at low concentrations, although there are strain dependent differences, 630Δerm biofilm level is significantly reduced $p<0.05$) in the 100 uM concentration of norspermidine, however, these biofilms developed in the presence of norspermidine, which may affect the growth rate at high concentrations. When the disassembly was performed in tissue culture flasks, the biofilm was not disrupted for 630Δerm.

Figure 16:
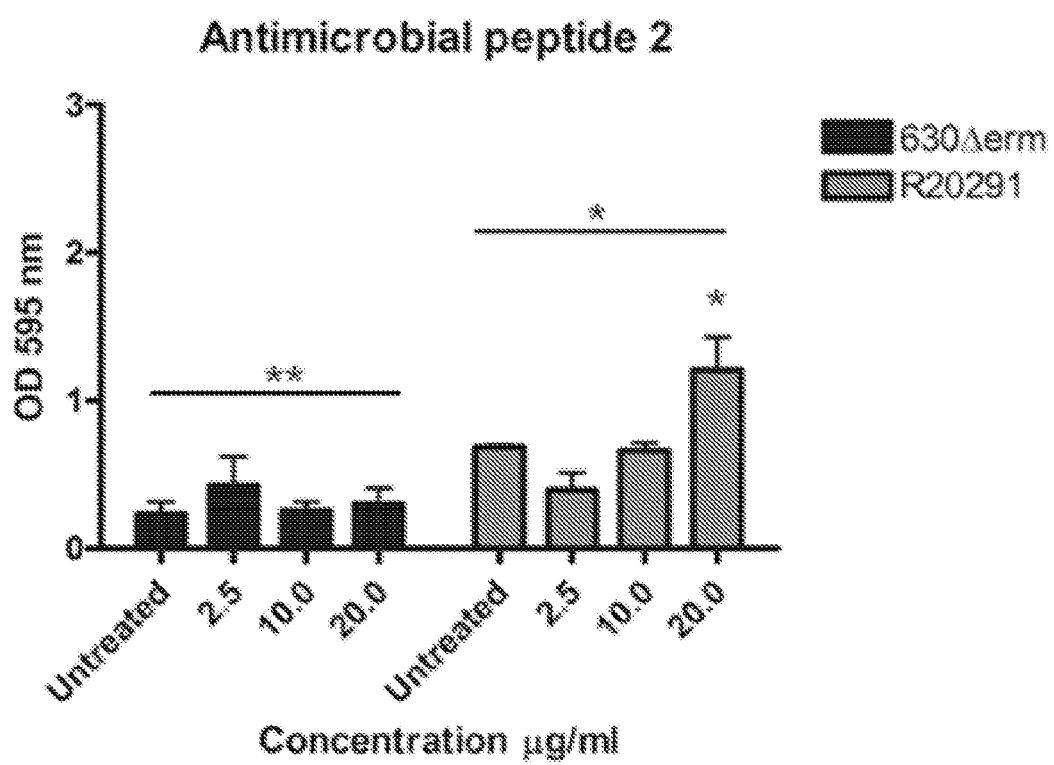

FIG. 16. Shows the effects of antimicrobial peptides on biofilm formation in *C. difficile* strains (light grey) 630Δerm and (dark grey) R20291.

Disassembly by cationic peptides—Biofilm formation by *P. aeruginosa, B. cenocepatia* and *L. monocytogenes* has been shown to be prevented using a cationic peptide; further Human beta-defensin 3—has been shown to inhibit biofilm formation in *S. aureus*. The two figures show that antimicrobial peptides 1 and 2 do not inhibit biofilm formation in *C. difficile*, and they do not disassemble biofilms. In fact, the concentration of antimicrobial peptide can actually enhance biofilm formation in *C. difficile*.

Figure 17:
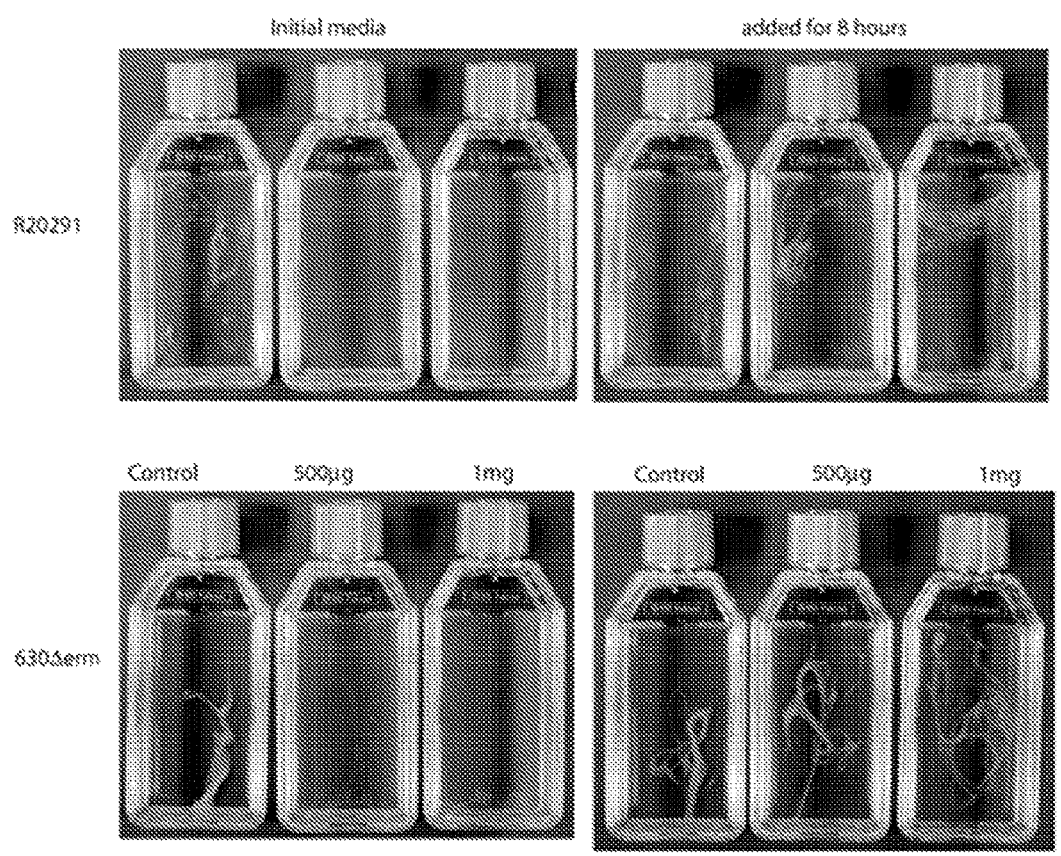

FIG. 17. Shows the formation of biofilms in *C. difficile* can be prevented by the addition of alginate lyase. When 500 μg and 1 mg of alginate lyase is added to the culture media the biofilm formation is inhibited.

Table 1. shows bacterial strains and plasmids used in the study.

Methods

Growth of Bacterial Strains

*C. difficile* strains used in this study are summarised in table 1. Strains were stored at −80° C. and were cultured on Braziers agar containing 4% egg-yolk, *C. difficile* supplement and 1% defibrinated horse blood or BHIS media (BHIS Oxoid with 0.5% w/v yeast and 0.1% L-cysteine). *Clostridium perfringens* NCTC 8237 strain, the control positive for biofilm formation assay, was cultured in blood agar. Liquid cultures were grown in BHIS broth (broth heart infusion) plus yeast extract (0.5%) and L-Cysteine (0.1%) (BHIS) and yeast peptone (YP) broth, 16 gL$^{-1}$ peptone, 10 gL$^{-1}$ yeast, and 5 gL$^{-1}$ NaCl$_2$. All cultures were grown in an anaerobic atmosphere (10% CO$_2$, 10% H$_2$, 80% N$_2$) at 37° C. *Escherichia coli* strain CA434, the conjugation donor, was grown in Luria-Bertani (LB) broth or agar supplemented with 12.5 μg/ml chloramphenicol.

Biofilm Formation and Visualization

*C. difficile* strains were grown on Brazier's agar for 2-3 days, and primary cultures were then inoculated using 3 single colonies into 10 ml pre-equilibrated BHIS and YP media. These were incubated for 16 h at 37° C., shaking at 65 r.p.m. These were inoculated with a 1/10 dilution into four different vessels to assess biofilm formation:

a) Liquid cultures in tissue culture flasks. Primary cultures were inoculated 1/10 into duplicate secondary cultures, one was incubated for 6 days statically and the other for 6 days on a shaking platform at 65 rpm. Tissue culture flasks were removed from the anaerobe hood and photographs were taken. Figures were compiled using Adobe Photoshop elements 8.0.

b) SEM and confocal Microscopy. For SEM, samples were processed from liquid cultures, in BHIS media, the supernatant removed carefully by pipetting, before 1 ml fixative (2.5% Paraformaldehyde/2.5% Glutaraldehyde/ 0.1M Sodium cacodylate pH 7.4) was added. The YP samples were centrifuged for 1 min 30 sec at 1500 rpm to pellet the micro-aggregates, before 1 ml fixative (2.5% Paraformaldehyde/2.5% Glutaraldehyde/0.1M Sodium cacodylate pH 7.4) was added. The samples were then processed in the microscopy unit, washed in 0.1 M Na cacodylate, post fixed in 1% osmium tetroxide/ 0.1M Na cacodylate, then stored in MilliQ water over night at 4° C. These were then dehydrated in 30%, 50%, 70%, 80%, 90% and 100% Ethanol. The samples were then mounted onto the aluminium stub and air-dried prior to Sputter coating. For samples in 24 well plates, circular glass 13 mm coverslips were placed in low evaporation 24 well plates, after which 2 mls of BHIS/ YP was carefully added. These were pre-equilibrated for 16 hours in an anaerobe chamber before inoculation with a 1/10 dilution from the primary cultures outlined about. The plates were sealed with Nescofilm® and incubated for 6 days at 37° C. The media was then removed and the wells were washed with 700 μl 1×PBS. For SEM analysis, fixative (2.5% Paraformaldehyde/ 2.5% Glutaraldehyde/0.1M Sodium cacodylate pH 7.4) was then added (500 μl per well) and samples were processed as outlined above. Confocal microscopy glass 13 mm coverslips and Thermanox coated 13 mm coverslips were washed in the wells with 1×PBS before 200 μl of stain was applied and incubated according to the manufacturer's guidelines. The stains used were Acridine orange and FilmTracer™ SYPRO® Ruby, Syto9 and Propidium iodide, and DAPI. These coverslips were mounted onto glass slides, a coverslip was applied over a 50% glycerol mounting media and these were sealed with clear nail varnish. The slides were visualised under oil immersion using a 40× objective using a laser confocal microscope. The excitation/emission used for these dyes were 488 nm/>560 nm respectively for SYPRO® Ruby stain and 543 nm/>560 nm Acridine orange. Single stains of Syto9 and Propidium iodide were performed to control for any cross bleed between channels, before these were used in combination, the excitation/emission was 488 nm/505-550 nm for Syto9 and 543 nm/>650 nm for Propidium iodide. *C. perfringens* NTCT 8237 was used as positive control and the assays were performed in quadruplicate. Images were analysed using Zeiss LSM image browser, and the images were compiled in Adobe Photoshop elements 8.0 c) Crystal violet assay; BHIS and YP media was pre-equilibrated for 16 hours in low evaporation 24 well plates prior to inoculation, with a 1/10 dilution of the overnight primary cultures. Bacteria were grown statically in 2 mls of BHIS/YP in 24-well plates for 6 days at 37° C. To prevent evaporation plates were sealed with Nescofilm®. The wells were then washed twice with 700 μl 1× PBS prior to incubation for 30 min at room temperature with 700 μl of filter-sterilized 1% crystal violet. Excess crystal violet was removed from the wells, followed by two washes with 1×PBS. The crystal violet was extracted by adding 700 μl methanol to each well and incubated for 15 min at room temperature. The OD595 was measured in a Spectrophotometer.

d) Glass tubes. BHIS/YP broth was added to glass tubes and pre-equilibrated for 16 hours prior to inoculation, with a 1/10 dilution of the overnight primary cultures. Samples were incubated for 6 days at 37° C., then removed from the anaerobe chamber and photographed. Images were compiled into figures using photoshop elements 8.0.

Degradation of the Biofilm

DNase, RNase and proteinase K digests were performed to determine the constituents of the biofilms. Liquid cultures of 630Δerm and R20291 incubated for 3 and 6 days were then treated by the addition of Bovine DNase, final concentration 1 mg/ml and 100 μg/ml, (10 mg stock dilutions were made in 0.15 M $NaCl_2$). RNaseA was added to a final concentration of 1 mg/ml and 100 μg/ml, (dilutions were made in nuclease free $dH_2O$). Proteinase K was added to a final concentration of 1 mg/ml (stock 20 mg/ml). Samples were incubated at room temperature for 15 minutes. Before and after addition of the DNase/RNase or Proteinase K, images were taken using a Canon 600D SLR, using a 50 mm prime lens mounted on a lighting rig. These images were compiled in photoshop Elements 8.0. To determine if biofilm formation could be inhibited in liquid culture, primary cultures of 630Δerm and R20291 were diluted 1/10 into TC flasks containing a low concentration of DNase (10 μg) or Proteinase K (10 μg), these samples were incubated statically and with shaking for 6 days before images were captured as outlined above.

DNase treatments were visualised by confocal microscopy; 630Δerm and R20291 were grown in 24 well plates for 6 days with thermanox coverslips, the media was removed and Bovine DNase was added to a final concentration of 1 mg, 100 μg, 10 μg and 1 μg, after a 15 minute incubation the DNase was removed and slides were washed with 1 ml 1×PBS. The untreated controls were incubated for 15 minutes with 0.15 M NaCl and washed with 1×PBS. These coverslips were mounted onto glass slides, a coverslip was applied over a 50% glycerol mounting media and these were sealed with clear nail varnish. The slides were visualised under oil immersion using a X40 objective using a laser confocal microscope (Zeiss microscope).

Disruption of biofilm by D-amino acids, norspermidine and alginate lyase.

Liquid cultures of 630Δerm and R20291 incubated for 3 days in 12 and 24 well plates, were then treated by the addition of D amino acids, at 3 μM D-tyrosine, 2 mM D-methionine, 5 mM D-tryptophan, 8.5 mM D-leucine, and then a mixture of each, (2.5 nM each D-amino acid above), Higher concentrations were also tested: D-leucine at 8.5 mM, 17 mM, 25 mM and, D-tryptophan at 5 mM, 10 mM, 25 mM and 50 mM. Norspermidine was also added into mature biofilm cultures (3 day old) at 15 μM, 25 μM, 50 μM and 100 μM. Antimicrobial peptides 1 and 2 were assessed for their ability to inhibit biofilm formation in 24 well plates, at a range of concentrations, 2.5 μg/ml, 10 μg/ml and 20 μg/ml.

Alginate lyase was added into mature biofilms (3 day old) at 500 μg and 1 mg. The effects on biofilm formation were also assessed by the addition of the above chemicals into the media when the cultures were inoculated.

Results

Biofilm Formation in Liquid Culture

Biofilm formation in *C. difficile* was assessed in different media under a range of conditions, including a variety of surfaces. The PCR ribotype 012 sequenced strain 630Δerm was analysed alongside the 027 PCR ribotype (R20291) and *C. perfringens* NCTC 8237. Strains were grown under static or shaking conditions in rich liquid media (BHIS) (FIG. 1) or non-rich media (YP) (FIG. 2) for 6 days. For *C. difficile* strains 630Δerm and R20291 biofilms were observed in BHIS broth in both shaking and static cultures, whereas for *C. perfringens* no obvious biofilms were observed and the media was turbid (FIG. 1). The appearance of the biofilms formed by the *C. difficile* isolates were distinctly different under the two different culture conditions analysed (FIGS. 1a & b). In static cultures the biofilm appear as a single distinct cloud like floc in a clear media (FIG. 1a), whereas in shaking cultures the biofilms appeared as multiple aggregates (FIG. 1a). The aggregates observed appear less dense in R20291 compared to 630Δerm, however the flocs and aggregates are not apparent in *C. perfringens* (FIG. 1). The biofilms observed in non-rich, YP broth were much smaller micro-aggregates (shaking conditions), and the flocs (static conditions) were apparent but not as stable as those formed in BHIS upon movement or agitation. The micro-aggregates were found predominantly attached to the side of the tissue culture flask under shaking conditions in the YP media (data not shown). Unlike other biofilm producing bacteria *C. difficile* does not form biofilms in glass tubes, termed pellicles, however sedimentation of the bacteria to the bottom of the tube was observed in both BHIS and YP media (data not shown).

Visualisation of Biofilm by SEM

SEM was used to visualise biofilm production in both liquid culture and attached to glass coverslips. Samples were analysed from both static cultures in BHIS and YP media (FIGS. 2a and b), as well as shaking cultures in both media (FIGS. 3a and b). The 150× magnification revealed the difference in density of the biofilms in BHIS compared to YP media in both shaking (FIG. 2a/b panel 1) and static (FIG. 3a/b panel 1) conditions. The biofilms formed in BHIS are larger and denser than the biofilms formed in YP media, which are visible as micro-aggregates. The 3000× magnification allows visualisation of the bacterial community and the matrix structure under static conditions for BHIS (FIG. 2a panel 2) and YP media (FIG. 2b panel 2), whereas under shaking conditions structure of the biofilms appear different. The individual bacteria are occluded by the density of the matrix in both BHIS (FIG. 3a panel 2 and 3) and YP shaking conditions (FIG. 3b panel 2 and 3). At 10,000× magnification the individual bacteria and their matrix connections are clearly visible in both BHIS (FIG. 2a, panel 3) and YP media (FIG. 2b, panel 3) in static culture. The filament connections between the bacteria and matrix are more apparent in BHIS media compared to YP (FIG. 2, panel 3). However, under shaking conditions, the 10,000× magnification reveals the individual bacteria and their matrix connections are not visible (FIG. 3a/b, panel 3).

The biofilms formed on glass cover slips were reduced (FIG. 4) compared with those formed in liquid media (FIGS. 1 and 2). The biofilms appeared to attach more efficiently to the plastic well in which the coverslips were incubated for 6 days, rather than to the glass coverslips. SEM images at 10,000× magnification reveal the matrix and bacteria are clearly visible in both BHIS (FIG. 4a-c) and YP (FIG. 4d-f) media; however there appear to be media specific and strain specific differences in the structure of the matrix and the bacteria. On glass coverslips the matrix appears multifarious for 630Δerm and R20291 in YP media (FIGS. 4d and e respectively) compared to BHIS (FIGS. 4a and b respectively). The bacteria appear to be longer for both 630Δerm (FIG. 4a/d) and R20291 (FIG. 4b/e) in YP media compared to the bacteria observed in BHIS media. Spores are present in R20291 BHIS (FIG. 5) at approximately 1-2 uM in size, and there is less visible matrix in this sample. The biofilms produced by *C. perfringens* also appear different in the various media; in BHIS media the majority of the sample is formed of coccoid shapes, with few rod shaped bacteria (FIG. 4c), whereas in YP media the majority of the sample is comprised of rod shaped bacteria joined by matrix (FIG. 4f). The matrix produced by *C. perfringens* is visually different from the matrix produced by *C. difficile* (FIG. 4d/e).

Visualisation of Biofilm Using Confocal Microscopy

Confocal microscopy with nucleic acid and protein specific stains was used to visualise the matrix produced by the *C. difficile* strain 630Δerm, and determine the constituents. Strain 630Δerm was grown for 6 days in 24 well plates containing glass coverslips in both BHIS and YP media. These coverslips were stained using Acridine orange (specific to nucleic acid) and SYPRO® Ruby (specific to proteins), then visualised by confocal microscopy (FIG. 5). The confocal images revealed that the EPS matrix formed by 630Δerm was comprised of both proteins (FIG. 5a/5c) and nucleic acid (FIG. 5b/5d), however the majority of the EPS matrix stained with the nucleic acid specific stain Acridine orange (FIG. 5b/5d). Once again consistent visual differences of the biofilms formed in BHIS media (FIG. 5a/5b) compared to YP (FIG. 5c/5d) were apparent. In BHIS media the biofilms are larger in diameter and more spread out than those formed in YP media (FIG. 5a-b, 4c-d respectively). To determine the proportion of live and dead bacteria in the EPS matrix, a live-dead stain was performed with propidium iodide and syto9 which revealed the majority of the matrix was comprised of live bacteria for both 630Δerm (FIG. 6a) and R20291 (FIG. 6b).

Composition and Degradation of the EPS Matrix

Confocal microscopy staining revealed that the majority of the matrix stained with the nucleic acid stain Acridine orange rather than the protein stain SYPRO® Ruby. To determine whether this was consistent with the constituents of the EPS matrix, digests with DNase, RNase A and proteinase K, were performed on the flocs produced in static culture by 630Δerm (FIG. 7). Degradation of the biofilm was observed in flask 2 and 3 (FIG. 7), which correspond to a 15 minute treatment with 1 mg/ml and 100 ug/ml DNase respectively, compared to Flask 1 the untreated control. RNase digestion of the floc produced by 630Δerm did not disrupt the biofilm at 1 mg/ml or 100 ug/ml flasks 4 and 5 (FIG. 7). A partial degradation with proteinase K was not observed (FIG. 7 flask 6) until the concentration was increased to 2 mg/ml proteinase K or the incubation time was increased to 24 hours (data not shown). The treatment with DNase, RNase A and proteinase K was reproducible with strain R20291 (FIG. 8), with degradation of the biofilm observed with both 1 mg/ml and 100 mg/ml DNase.

Inhibition of biofilm formation in TC flasks was performed by the addition of a low concentration of DNase (10 μg/ml) prior to inoculation of the media (FIG. 9). After a 6 day incubation under static and shaking conditions the media was turbid, indicating bacterial growth, but no flocs or aggregates were observed. This was compared to the untreated control and a low concentration of proteinase K (10 μg/ml) added prior to inoculation, in which flocs and aggregates were observed. However the flocs and aggregates observed in the media containing proteinase K, appeared smaller in the case of the aggregates and less dense in the case of the floc than those in the untreated control (FIG. 9).

Visualisation of the DNase Treatment by Confocal Microscopy

Strains 630Δerm and R20291 were grown in 24 well plates on both glass and thermanox coverslips (plastic coated). Biofilm formation was superior on the thermanox coverslips in both BHIS and YP media (FIG. 10). Degradation of the biofilms was performed by incubating the coverslips in the 24 well plate with DNase for 15 minutes before visualisation by confocal microscopy. The biofilms were absent in the DNase treatment for both BHIS (FIG. 10b) and YP media (FIG. 10d), compared to the untreated controls (FIGS. 10a and 10c). The z-stack produced with the controls reveals that the biofilm formed in BHIS (FIG. 10a) is thicker in YP media (FIG. 10c). This observation was reproduced in strains R20291 (data not shown). The degradation of the C. difficile biofilm was dose dependent, whereby at 10 ug (FIG. 11c) and more notably 1 ug DNase (FIG. 11d), incomplete degradation of the biofilm was observed.

Use of Agents to Degrade Biofilm

Additional compounds were assessed for their ability to disrupt and inhibit biofilm formation. The effects of certain D-amino acids on the integrity and formation of biofilm formation was assessed using a wide variety of concentrations. At low concentrations the biofilm formation and stability was unaffected by D-amino acids tested (FIG. 12). The effects of high concentrations of D-amino acids were to increase the biofilm formation (FIG. 13), with the exception of 50 mM in strain 630derm, as this concentration completely inhibited growth by disassembling the preformed biofilms. D-tryptohpan also increased the biofilm formation in strain R20291 at all concentrations tested, and at high concentrations in strain 630Δerm (FIG. 14). Norspermidine and D-amino acids are produced naturally by B. subtilis to disassemble biofilms, however, the addition of norspermidine to biofilm cultures actually enhances the biofilm formation in the hypervirulent outbreak strains R20291. There is a slight decrease in viability in strain 630Δerm at the highest concentration of norspermidine (FIG. 15). This indicates that there are strain dependent differences to the treatment with D-amino acids and norspermidine, however, none of these successfully disrupt the C. difficile biofilm. Antimicrobial peptides are cationic peptides, which have been shown to disrupt DNA, however, when such peptides were tested against C. difficile (FIG. 16) the effect was to enhance rather than inhibit the formation of the biofilm. The effect of alginate lyase on inhibiting and disrupting biofilm formation was also assessed. It is clear that alginate lyase can inhibit biofilm formation in strains R20291 and 630Δerm, however, it does not break down existing mature biofilms (FIG. 17).

Summary

The main findings of this study can be summarised as follows:

We have unequivocally demonstrated that C. difficile form biofilms in vitro in both liquid broth and on surfaces. Through evaluation of biofilm formation in numerous C. difficile clinical isolates, we have shown that the bacteria and the extracellular polymeric substance (EPS) matrix comprising the biofilm are clearly visible by both scanning electron microscopy and confocal microscopy. The super-structure and sub-structures of these biofilms and their compositions differ dependent upon the strain of bacteria and environmental conditions, such as nutrient availability and the specific growth parameters. Notably, unlike some bacteria, our evidence shows C. difficile are most likely to form biofilms in nutrient rich conditions, and matrix formation may therefore represent a mechanism to avoid sporulation in order to colonise a host before the transmission phase of the infection.

We have found that in both rich and non-rich media C. difficile biofilms are formed primarily of nucleic acid, polysaccharides, and proteins. Importantly, however, we have found that under all conditions tested the major component of the EPS matrix is nucleic acid, namely DNA, combined with some protein. Furthermore, we have shown that the biofilm of C. difficile is disrupted in a dose dependent manner by DNase treatment, whereas RNase A and proteinase K digestion have less effect on the biofilm structural integrity. Unlike some bacteria, a large proportion of the biofilm is comprised of live bacteria.

C. difficile biofilms are heterogenous and comprise live bacteria. These properties contribute to the virulence of the disease.

Bacterial biofilms can be disrupted by a number of different compounds, depending on the bacteria and the components of the matrix. It has been shown that B. subtilis produces D-amino acids and norspermidine to target components of the biofilm, and to promote dispersal of the biofilm, however when these compounds are tested in C. difficile, they have little or no effect on biofilm formation or the dispersal of the C. difficile biofilm. Antimicrobial peptides have also been shown to have an inhibitory effect on biofilm formation; however it appears that the antimicrobial peptides tested against C. difficile actually enhance biofilm formation at subinhibitory concentrations.

Alginate lyase has been shown to inhibit biofilm formation in pseudomonas aeruginosa (Alkawash et al) and it has been proposed that P. aeruginosa produce alginate lyase to promote biofilm dispersal, by dispersal of the exopolysaccharide (alginate). It was thought that this dispersal was an enzymatic degradation, however, there is a recent paper that suggests alginate lyase disrupts biofilms in a catalyse independent manor (Lamppa et al.,). It is unclear whether C. difficile biofilms are comprised of alginate. However, the addition of alginate lyase to the culture medium prevents the formation of these biofilms, but does not disrupt mature biofilms.

Notably, specific degradation of C. difficile biofilm by DNase treatment in a dose dependent manner provides a method by which the virulence of the bacteria can be reduced, limiting its ability to colonize the host to cause infection and also improves its susceptibility to other cytotoxic compounds. This therefore represents a new clinical avenue and potential therapeutic target in the treatment of C. difficile infection.

TABLE 1

| Strains | Characteristics | Source |
| --- | --- | --- |
| 630Δerm | An erythromycin derivative of C. difficle 630, PCR ribotype 012 | Hussain et al., 2005 |
| R20291 | Hypervirulent PCR ribotype 027, isolated from an outbreak in 2004-2004 | Stabler et al., 2009 |
| C. perfringens | strain NCTC 8237 | Peter Donachie |

REFERENCES

Flemming, H. C. & Wingender, J. (2010) The biofilm matrix. Nat Rev Microbiol. 8(9): 623-33.

Reynolds, C. B, Emerson, J. E., de la Riva, L., Fagan, R. P. & Fairweather, N. F. (2011) The Clostridium difficile Cell Wall Protein CwpV is Antigenically Variable between Strains, but Exhibits Conserved Aggregation-Promoting Function. PLoS Pathogens, 7(4): e1002024.

Rupnik, M., Wilcox, M. H. & Gerding, D. N. (2009) Clostridium difficile infection: new developments in epidemiology and pathogenesis. Nat Rev Microbiol. 7: 526-536.

Lamppa J W, Griswold K E: Alginate lyase exhibits catalysis-independent biofilm dispersion and antibiotic synergy. Antimicrob Agents Chemother 2013, 57(1):137-145.

Alkawash M A, Soothill J S, Schiller N L: Alginate lyase enhances antibiotic killing of mucoid Pseudomonas

*aeruginosa* in biofilms. *APMIS: acta pathologica, microbiologica, et immunologica Scandinavica* 2006, 114(2): 131-138.

The invention claimed is:

1. A method of treating *Clostridium difficile* biofilm formation in a mammal, comprising administering to said mammal an effective amount of a DNase I deoxyribonuclease or a functional fragment thereof, thereby degrading the *Clostridium difficile* biofilm.
2. The method according to claim 1 wherein said mammal is a primate.
3. The method according to claim 1 wherein said mammal is human, equine, canine, feline, porcine, ovine, ungulate or any other domestic or agricultural species.
4. The method of claim 1, wherein said functional fragment comprises at least the catalytic unit of said deoxyribonuclease.
5. The method of claim 1, wherein said deoxyribonuclease is mammalian.
6. The method of claim 5, wherein said deoxyribonuclease is selected from the group comprising: human, bovine, porcine, ovine, feline, canine, equine, and ungulate.
7. The method of claim 6, wherein said deoxyribonuclease is human or bovine.
8. The method of claim 1, wherein said deoxyribonuclease is a recombinant molecule.
9. The method of claim 1, wherein said deoxyribonuclease degrades *C. difficile* biofilm.
10. The method of claim 1, further comprising administering at least one therapeutic agent effective against *C. difficile*.
11. The method of claim 10, wherein the at least one therapeutic agent effective against *C. difficile* comprises an antibiotic, antibody therapeutic, or a cytotoxic agent.

* * * * *